United States Patent
Schäefer et al.

[11] Patent Number: 5,958,837
[45] Date of Patent: Sep. 28, 1999

[54] SUBSTITUTED 2-PHENYLPYRIDINES

[75] Inventors: Peter Schäefer, Ottersheim; Gerhard Hamprecht, Weinheim; Elisabeth Heistracher, Ludwigshafen; Ralf Klintz, Gruenstadt; Hartmann König, Heidelberg; Helmut Walter, Obrigheim; Karl-Otto Westphalen, Speyer; Ulf Misslitz, Neustadt, all of Germany

[73] Assignee: BASF Aktiengesellschaft, Ludwigshafen, Germany

[21] Appl. No.: 08/849,874

[22] PCT Filed: Jan. 4, 1996

[86] PCT No.: PCT/EP96/00022

§ 371 Date: Jun. 18, 1997

§ 102(e) Date: Jun. 18, 1997

[87] PCT Pub. No.: WO96/21647

PCT Pub. Date: Jul. 18, 1996

[30] Foreign Application Priority Data

Jan. 13, 1995 [DE] Germany .................. 195 00 760

[51] Int. Cl.[6] .................. C07D 211/70; A01N 43/40
[52] U.S. Cl. .................. 504/244; 504/225; 504/248; 504/252; 504/260; 546/339; 546/276.4; 546/194; 544/124
[58] Field of Search .................. 504/244, 225, 504/248, 252, 260; 546/339, 276.4, 194; 544/124

[56] References Cited

U.S. PATENT DOCUMENTS

| | | | |
|---|---|---|---|
| 4,005,201 | 1/1977 | Yurugi | 424/248 |
| 4,331,597 | 5/1982 | Makabe | 546/288 |
| 4,393,058 | 7/1983 | Makabe | 424/246 |
| 4,559,354 | 12/1985 | Fuhrer | 514/357 |
| 4,920,119 | 4/1990 | Attwood | 514/243 |
| 4,943,385 | 7/1990 | Inoue | 252/299 |
| 5,204,476 | 4/1993 | Wachtler | 546/290 |
| 5,230,827 | 7/1993 | Reiffenrath | 252/299 |
| 5,407,599 | 4/1995 | De Meijere | 252/299 |

FOREIGN PATENT DOCUMENTS

| | | |
|---|---|---|
| 2082304 | 6/1992 | Canada . |
| 267 670 | 5/1988 | European Pat. Off. . |
| 283 326 | 9/1988 | European Pat. Off. . |
| 463 492 | 1/1992 | European Pat. Off. . |
| 251 206 | 7/1986 | Germany . |
| 42 36 103 | 10/1992 | Germany . |
| 4323916 | 7/1993 | Germany . |
| 63048254 | 8/1986 | Japan . |
| 63254182 | 4/1987 | Japan . |
| 63313768 | 6/1987 | Japan . |
| 01066161 | 9/1987 | Japan . |
| 01070455 | 9/1987 | Japan . |
| 05331143 | 5/1992 | Japan . |
| 92/06085 | 4/1992 | WIPO . |
| 94/10105 | 5/1994 | WIPO . |
| 94/26720 | 11/1994 | WIPO . |

OTHER PUBLICATIONS

Yurugi et al. CA 84:31110, 1976.
Byron et al. CA 94: 183690, 1981.
*Mol. Crys. Liq. Cryst.,* 62 (1–2), 103–114, 1980.
*J. Chem. Res.,* Synop., 3, 86, 1994.
*Izv. Timiryazevsk. S.–Kh. Akad.,* 3, 155–160, 1990.
*Chem. Abst.,* 114, 11, AN 96724k.

*Primary Examiner*—Jane Fan
*Attorney, Agent, or Firm*—Keil & Weinkauf

[57] ABSTRACT

Substituted 2-phenylpyridines I

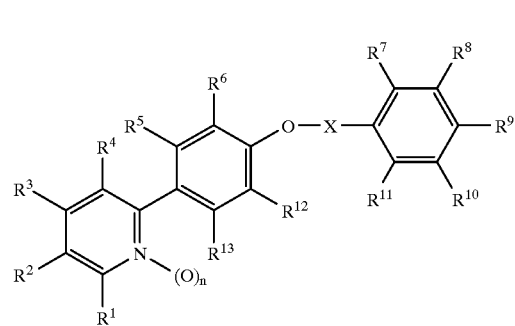

wherein all variables are as defined in the specification are used as herbicides and for the desiccation/defoliation of plants.

6 Claims, No Drawings

SUBSTITUTED 2-PHENYLPYRIDINES

This is a 371 of PCT/EP96/00022 filed Jan. 4, 1996 now WO 96/21647 Jul. 18, 1996.

The present invention relates to novel substituted 2-phenylpyridines of the formula I

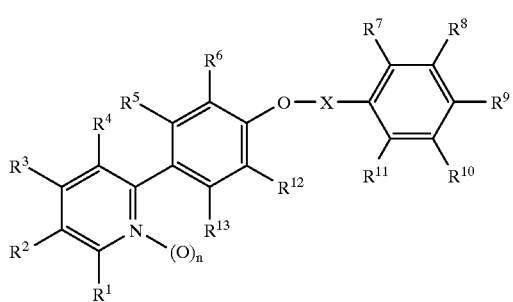

where the variables have the following meanings:

n is 0 or 1;

$R^1$, $R^3$, $R^4$ independently of one another are
hydrogen, halogen, $C_1$–$C_4$-alkyl, $C_1$–$C_4$-haloalkyl, hydroxyl, $C_1$–$C_4$-alkoxy, $C_1$–$C_4$-haloalkoxy, nitro, amino, $C_1$–$C_4$-alkylamino, di($C_1$–$C_4$-alkyl)amino, mercapto, $C_1$–$C_4$-alkylthio, $C_1$–$C_4$-haloalkylthio, cyano, hydroxycarbonyl, ($C_1$–$C_4$-alkoxy)carbonyl, aminocarbonyl, $C_1$–$C_4$-alkylaminocarbonyl or di($C_1$–$C_4$-alkyl)aminocarbonyl;

$R^2$ is hydrogen, halogen, $C_1$–$C_4$-alkyl, $C_1$–$C_4$-haloalkyl, cyano, nitro, amino, hydroxyl, $C_1$–$C_4$-haloalkoxy, mercapto, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;

$R^5$ is hydrogen, halogen or cyano;

$R^6$ and $R^{13}$ independently of one another are hydrogen or halogen;

X is methylene or carbonyl;

$R^7$, $R^8$, $R^9$, $R^{10}$ independently of one another are hydrogen, halogen, $C_1$–$C_4$-alkyl, $C_1$–$C_4$-alkoxy or nitro;

$R^{11}$ is hydrogen, halogen, $C_1$–$C_4$-alkyl, $C_1$–$C_4$-haloalkyl, $C_1$–$C_4$-hydroxyalkyl, $C_1$–$C_4$-alkoxy-$C_1$–$C_4$-alkyl, $C_3$–$C_6$-cycloalkyl, $C_2$–$C_4$-alkenyl, $C_2$–$C_4$-alkynyl, hydroxycarbonyl-$C_1$–$C_4$-alkyl, hydroxycarbonyl-$C_2$–$C_4$-alkenyl, hydroxycarbonyl-$C_2$–$C_4$-alkynyl, ($C_1$–$C_4$-alkoxy)carbonyl-$C_1$–$C_4$-alkyl, ($C_1$–$C_4$-alkoxy)carbonyl-$C_2$–$C_4$-alkenyl, ($C_1$–$C_4$-alkoxy)carbonyl-$C_2$–$C_4$-alkynyl, ($C_1$–$C_4$-alkoxy)carbonyl-$C_2$–$C_4$-haloalkyl, ($C_1$–$C_4$-alkoxy)carbonyl-$C_2$–$C_4$-haloalkenyl, aminocarbonyl-$C_1$–$C_4$-alkyl, aminocarbonyl-$C_2$–$C_4$-alkenyl, aminocarbonyl-$C_2$–$C_4$-alkynyl, $C_1$–$C_4$-alkylaminocarbonyl-$C_1$–$C_4$-alkyl, $C_1$–$C_4$-alkylaminocarbonyl-$C_2$–$C_4$-alkenyl, $C_1$–$C_4$-alkylaminocarbonyl-$C_2$–$C_4$-alkynyl, di($C_1$–$C_4$-alkyl)aminocarbonyl-$C_1$–$C_4$-alkyl, di($C_1$–$C_4$-alkyl)aminocarbonyl-$C_2$–$C_4$-alkenyl, di($C_1$–$C_4$-alkyl)aminocarbonyl-$C_2$–$C_4$-alkynyl, aminocarbonyl-$C_1$–$C_4$-haloalkyl, aminocarbonyl-$C_2$–$C_4$-haloalkenyl, $C_1$–$C_4$-alkylaminocarbonyl-$C_1$–$C_4$-haloalkyl, $C_1$–$C_4$-alkylaminocarbonyl-$C_2$–$C_4$-haloalkenyl, di($C_1$–$C_4$-alkyl)aminocarbonyl-$C_2$–$C_4$-haloalkyl, di($C_1$–$C_4$-alkyl)aminocarbonyl-$C_2$–$C_4$-haloalkenyl, (hydroxycarbonyl-$C_1$–$C_4$-alkyl)aminocarbonyl-$C_2$–$C_4$-alkenyl, (hydroxycarbonyl-$C_1$–$C_4$-alkyl)aminocarbonyl-$C_2$–$C_4$-haloalkenyl, N-(hydroxycarbonyl-$C_1$–$C_4$-alkyl)-N-($C_1$–$C_4$-alkyl)aminocarbonyl-$C_2$–$C_4$-alkenyl, N-(hydroxycarbonyl-$C_1$–$C_4$-alkyl)-N-($C_1$–$C_4$-alkyl)aminocarbonyl-$C_2$–$C_4$-haloalkenyl, [($C_1$–$C_4$-alkoxy)carbonyl-$C_1$–$C_4$-alkyl]aminocarbonyl-$C_2$–$C_4$-alkenyl, [($C_1$–$C_4$-alkoxy)carbonyl-$C_1$–$C_4$-alkyl]aminocarbonyl-$C_2$–$C_4$-haloalkenyl, N-[($C_1$–$C_4$-alkoxy)carbonyl-$C_1$–$C_4$-alkyl]-N-($C_1$–$C_4$-alkyl)aminocarbonyl-$C_2$–$C_4$-alkenyl, N-[($C_1$–$C_4$-alkoxy)carbonyl-$C_1$–$C_4$-alkyl]-N-($C_1$–$C_4$-alkyl)aminocarbonyl-$C_2$–$C_4$-haloalkenyl, 2-[($C_1$–$C_4$-alkoxy)carbonyl]-pyrrolidin-1-yl-carbonyl-$C_2$–$C_4$-alkenyl, 2-[($C_1$–$C_4$-alkoxy)carbonyl]pyrrolidin-1-ylcarbonyl-$C_2$–$C_4$-haloalkenyl, formyl, ($C_1$–$C_4$-alkyl)carbonyl, ($C_1$–$C_4$-haloalkyl)carbonyl, hydroxyimino-$C_1$–$C_4$-alkyl, $C_1$–$C_4$-alkoxyimino-$C_1$–$C_4$-alkyl, 1,1-di($C_1$–$C_4$-alkoxy)-$C_1$–$C_4$-alkyl, 1,1-di($C_1$–$C_4$-alkylthio)-$C_1$–$C_4$-alkyl, nitro, hydroxylamino, amino, $C_1$–$C_4$-alkylamino, $C_3$–$C_6$-cycloalkylamino, di($C_1$–$C_4$-alkyl)amino, ($C_1$–$C_4$-alkyl)carbonylamino, ($C_1$–$C_4$-haloalkyl)carbonylamino, $C_1$–$C_4$-alkylsulfonylamino, di($C_1$–$C_4$-alkylsulfonyl)amino, $C_1$–$C_4$-haloalkylsulfonylamino, hydroxyl, $C_1$–$C_4$-alkoxy, $C_1$–$C_4$-haloalkoxy, cyano-$C_1$–$C_4$-alkoxy, $C_1$–$C_4$-alkoxy-$C_1$–$C_4$-alkoxy, $C_1$–$C_4$-alkylthio-$C_1$–$C_4$-alkoxy, $C_3$–$C_6$-cycloalkoxy, $C_2$–$C_4$-alkenyloxy, $C_2$–$C_4$-alkynyloxy, hydroxycarbonyl-$C_1$–$C_4$-alkoxy, ($C_1$–$C_6$-alkoxy)carbonyl-$C_1$–$C_4$-alkoxy, $C_1$–$C_4$-alkoxy-($C_1$–$C_4$-alkoxy)carbonyl-$C_1$–$C_4$-alkoxy, ($C_1$–$C_4$-alkoxy)carbonyl-($C_1$–$C_4$-alkoxy)carbonyl-$C_1$–$C_4$-alkoxy, aminocarbonyl-$C_1$–$C_4$-alkoxy, $C_1$–$C_4$-alkylaminocarbonyl-$C_1$–$C_4$-alkoxy, di($C_1$–$C_4$-alkyl)aminocarbonyl-$C_1$–$C_4$-alkoxy, 1-pyrrolidinylcarbonyl-$C_1$–$C_4$-alkoxy, 1-piperidinyl-carbonyl-$C_1$–$C_4$-alkoxy, 4-morpholinyl-carbonyl-$C_1$–$C_4$-alkoxy, aminocarbonyl-($C_1$–$C_4$-alkoxy)carbonyl-$C_1$–$C_4$-alkoxy, ($C_1$–$C_4$-alkyl)aminocarbonyl-($C_1$–$C_4$-alkoxy)carbonyl-$C_1$–$C_4$-alkoxy, di($C_1$–$C_4$-alkyl)aminocarbonyl-($C_1$–$C_4$-alkoxy)carbonyl-$C_1$–$C_4$-alkoxy, 1-pyrrolidinyl-carbonyl-($C_1$–$C_4$-alkoxy)carbonyl-$C_1$–$C_4$-alkoxy, 1-piperidinylcarbonyl-($C_1$–$C_4$-alkoxy)carbonyl-$C_1$–$C_4$-alkoxy, 4-morpholinylcarbonyl-($C_1$–$C_4$-alkoxy)carbonyl-$C_1$–$C_4$-alkoxy, [($C_1$–$C_4$-alkoxy)carbonyl-$C_1$–$C_4$-alkyl]aminocarbonyl-$C_1$–$C_4$-alkoxy, N-[($C_1$–$C_4$-alkoxy)carbonyl-$C_1$–$C_4$-alkyl]-N-($C_1$–$C_4$-alkyl)aminocarbonyl-$C_1$–$C_4$-alkoxy, [2-[($C_1$–$C_4$-alkoxy)carbonyl]pyrrolidin-1-yl]carbonyl-$C_1$–$C_4$-alkoxy, cyano, hydroxycarbonyl, COCl, ($C_1$–$C_4$-alkoxy)carbonyl, ($C_1$–$C_4$-haloalkoxy)carbonyl, $C_1$–$C_4$-alkoxy-($C_1$–$C_4$-alkoxy)carbonyl, aminocarbonyl, $C_1$–$C_4$-alkylaminocarbonyl, di($C_1$–$C_4$-alkyl)aminocarbonyl, $C_3$–$C_6$-cycloalkylaminocarbonyl, 1-pyrrolidinylcarbonyl, 1-piperidinyl-carbonyl, 4-morpholinylcarbonyl, hydroxycarbonyl-$C_1$–$C_4$-alkylaminocarbonyl, N-(hydroxycarbonyl-$C_1$–$C_4$-alkyl)-N-($C_1$–$C_4$-alkyl)aminocarbonyl, ($C_1$–$C_4$-alkoxy)carbonyl-$C_1$–$C_4$-alkylaminocarbonyl, N-[($C_1$–$C_4$-alkoxy)carbonyl-$C_1$–$C_4$-alkyl]-N-($C_1$–$C_4$-alkyl)aminocarbonyl, 2-hydroxycarbonylpyrrolidin-1-yl-carbonyl, 2-[($C_1$–$C_4$-alkoxy)carbonyl]pyrrolidin-1-yl-carbonyl or a group

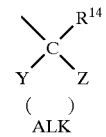

where
Y and Z independently of one another are oxygen or sulfur, $R^{14}$ is hydrogen, $C_1$–$C_4$-alkyl or ($C_1$–$C_4$-alkoxy)carbonyl and Alk is an ethylene or trimethylene chain where one or more hydrogen atoms can be replaced in each case by $C_1$–$C_4$-alkyl or ($C_1$–$C_4$-alkoxy)carbonyl;

$R^{12}$ is hydrogen, nitro, amino, hydroxylamino, $C_1$–$C_4$-alkylsulfonylamino, di($C_1$–$C_4$-alkylsulfonyl)amino, $C_1$–$C_4$-haloalkylsulfonylamino, ($C_1$–$C_4$-alkoxy)carbonyl-$C_1$–$C_4$-haloalkyl or ($C_1$–$C_4$-alkoxy)carbonyl-$C_2$–$C_4$-haloalkenyl;

with the proviso that $R^5$, $R^7$, $R^{11}$ and $R^{13}$ are not all simultaneously hydrogen or $R^7$ and $R^8$ or $R^{10}$ and $R^{11}$ are not simultaneously fluorine, and, if applicable, the agriculturally useful salts of the compounds I.

The invention furthermore relates to the use of compounds I' where I' corresponds to the definition I without the proviso as herbicides and/or for desiccating and/or defoliating plants, herbicidal composition and compositions for desiccating and/or defoliating plants which comprise the compounds I' as active ingredients, method of controlling undesirable vegetation and of desiccating and/or defoliating plants using the compounds I', processes for the preparation of the compounds I and of herbicidal compositions and compositions for desiccating and/or defoliating plants using the compounds I', and the use of intermediates II for the preparation of the compounds I.

2-Phenylpyridines of the type of the compounds I have previously been described in the literature as liquid crystals and pharmaceuticals. For example, liquid crystals whose general formulae also fall within the scope of 2-phenylpyridines are the subject-matter of the following publications: DE-A 38 07 955, DE-A 39 15 804, DE-A 42 36 103, EP-A 283 326, EP-A 433 826, EP-A 541 081, JP-A 63/048 254, JP-A 63/254 182, JP-A 63/313 768, JP-A 01/066 161, JP-A 01/070 455, JP-A 05/331 143 and Mol. Cryst. Liq. Cryst. 62(1–2), (1980) 103–114.

2-Phenylpyridines which have a pharmacological action can be found, for example, in DE-A 25 12 673, DE-A 30 35 259, BE-A 885 484, EP-A 274 654, EP-A 039 892 and WO 92/06085.

2-Phenylpyridines whose structure is similar to the compounds I have furthermore been described in DD-A 251 206, in J. Chem. Res., Synop. 3, (1994) 86, and Izv. Timiryazevsk. S-Kh. Akad. 3, (1990) 155–160.

Finally, the earlier German Application DE-A 43 23 916 discloses that certain 2-(4-hydroxyphenyl)pyridines, inter alia the compounds of the formula II'

II' where
$R^{2'}$ is halogen, cyano, nitro, $C_1$–$C_4$-alkyl, $C_1$–$C_4$-haloalkyl, $C_1$–$C_4$-haloalkoxy, $C_1$–$C_4$-alkylthio or $C_1$–$C_4$-haloalkylthio;

$R^{4'}$ is hydrogen, nitro, amino, cyano, hydroxyl, mercapto, hydroxycarbonyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di($C_1$–$C_4$-alkyl)amino, $C_1$–$C_4$-alkylthio, $C_1$–$C_4$-haloalkylthio or ($C_1$–$C_4$-alkoxy)carbonyl;

$R^{5'}$ is hydrogen or halogen and $R^{12'}$ is nitro, amino, $C_1$–$C_4$-alkylsulfonylamino, di($C_1$–$C_4$-alkylsulfonyl)amino, $C_1$–$C_4$-haloalkylsulfonylamino, ($C_1$–$C_4$-alkoxy)carbonyl-CH(halogen)—$CH_2$—, ($C_1$–$C_4$-alkoxy)carbonyl-C(halogen)=CH—, ($C_1$–$C_4$-alkoxy)carbonyl-CH=C(halogen)— or ($C_1$–$C_4$-alkoxy)carbonyl-C(halogen)=C (halogen)— has a herbicidal and desiccant/defoliant action.

However, the herbicidal action, of the known compounds, against the harmful plants is not always fully satisfactory.

It was therefore an object of the present invention to provide novel herbicidally active compounds which allow better tailored control of undesirable plants than this was possible to date. The object also extends to the provision of novel compounds which act as desiccants/defoliants.

Accordingly, we have found the substituted 2-phenylpyridines of the formula I or I' defined at the outset, and their herbicidal action. We have furthermore found herbicidal compositions which comprise the compounds I' and which have a very good herbicidal action. We have furthermore found processes for the preparation of these compositions and methods of controlling undesirable vegetation using the compounds I'.

Furthermore, we have found that the compounds I' are also suitable for defoliating and desiccating parts of plants, suitable plants being crop plants such as cotton, potatoes, oilseed rape, sunflower, soya beans or field beans, in particular cotton. Accordingly, we have found compositions for desiccating and/or defoliating plants, processes for the preparation of these compositions and methods of desiccating and/or defoliating plants using the compounds I.

Depending on the substitution pattern, the compounds of the formula I can have one or more chiral centers, in which case they are present as enantiomer or diastereomer mixtures. The present invention relates to the pure enantiomers or diastereomers and also to their mixtures.

The substituted 2-phenylpyridines I can exist in the form of their agriculturally useful salts, the type of salt generally not being critical. In general, suitable salts are salts of those bases and those acid addition salts in which the herbicidal action is not adversely affected in comparison with the free compound I.

Particularly suitable basic salts are the salts of the alkali metals, preferably sodium and potassium salts, of the alkaline earth metals, preferably calcium and magnesium salts, those of the transition metals, preferably zinc and iron salts, and ammonium salts, where, if desired, the ammonium ion can have attached to it one to three $C_1$–$C_4$-alkyl, hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl(2-hydroxyethyl)ammonium salts, furthermore phosphonium salts, sulfonium salts, preferably tri($C_1$–$C_4$-alkyl)sulfonium salts, and sulfoxonium salts, preferably tri($C_1$–$C_4$-alkyl)sulfoxonium salts.

Amongst the acid addition salts, particular mention may be made of the hydrochlorides and hydrobromides, sulfates, nitrates, phosphates, oxalates and the dodecylbenizenesulfonates.

The organic moieties mentioned for the substituents $R^1$ to $R^{14}$ or as radicals on these substituents or on the Alk chain are, as is the meaning halogen, collective terms for individual enumerations of each of the group members. All carbon chains, ie. all alkyl, haloalkyl, hydroxyalkyl, alkoxy, cyanoalkoxy, alkylthio, alkylsulfinyl, alkylsulfonyl, haloalkoxy, haloalkylthio, haloalkylsulfonyl, alkylamino, dialkylamino, alkylcarbonyl, haloalkylcarbonyl, alkoxycarbonyl, alkylaminocarbonyl, dialkylaminocarbonyl, aminocarbonylalkyl, alkenyl, haloalkenyl, alkynyl, alkenyloxy, alkynyloxy, hydroxycarbonylalkyl, hydroxycarbonylalkoxy, hydroxycarbonylalkenyl, hydroxycarbonylalkynyl, hydroxyiminoalkyl, aminocarbonylalkoxy, aminocarbonylalkenyl or aminocarbonylalkynyl moieties can be straight-chain or branched. Halogenated substituents preferably have attached to them one to five identical or different halogen atoms.

For example, specifically, halogen is: fluorine, chlorine, bromine or iodine;

$C_1$–$C_4$-alkyl and the alkyl moities of $C_1$–$C_4$-alkoxy-$C_1$–$C_4$-alkyl, $C_1$–$C_4$-alkylaminocarbonyl-$C_1$–$C_4$-alkyl, $C_1$–$C_4$-alkylaminocarbonyl-$C_2$–$C_4$-alkenyl, $C_1$–$C_4$-alkylaminocarbonyl-$C_2$–$C_4$-alkynyl, N-(hydroxycarbonyl-$C_1$–$C_4$-alkyl)-N-($C_1$–$C_4$-alkyl) aminocarbonyl-$C_2$–$C_4$-alkenyl, N-(hydroxycarbonyl-$C_1$–$C_4$-alkyl)-N-($C_1$–$C_4$-alkyl)aminocarbonyl-$C_2$–$C_4$-haloalkenyl, [($C_1$–$C_4$-alkoxy)carbonyl-$C_1$–$C_4$-alkyl] aminocarbonyl-$C_2$–$C_4$-alkenyl, N-[($C_1$–$C_4$-alkoxy) carbonyl-$C_1$–$C_4$-alkyl]-N-($C_1$–$C_4$-alkyl)aminocarbonyl-$C_2$–$C_4$-alkenyl, [($C_1$–$C_4$-alkoxy)carbonyl-$C_1$–$C_4$-alkyl] aminocarbonyl-$C_2$–$C_4$-haloalkenyl, N-[($C_1$–$C_4$-alkoxy) carbonyl-$C_1$–$C_4$-alkyl]-N-($C_1$–$C_4$-alkyl)aminocarbonyl-$C_2$–$C_4$-haloalkenyl, $C_1$–$C_4$-alkoxyimino-$C_1$–$C_4$-alkyl, 1,1-di($C_1$–$C_4$-alkoxy)-$C_1$–$C_4$-alkyl, 1,1-di($C_1$–$C_4$-alkylthio)-$C_1$–$C_4$-alkyl, [($C_1$–$C_4$-alkoxy)carbonyl-$C_1$–$C_4$-alkyl]aminocarbonyl-$C_1$–$C_4$-alkoxy, N-[($C_1$–$C_4$-alkoxy)carbonyl-$C_1$–$C_4$-alkyl]-N-($C_1$–$C_4$-alkyl) aminocarbonyl-$C_1$–$C_4$-alkoxy and N-(hydroxycarbonyl-$C_1$–$C_4$-alkyl)-N-($C_1$–$C_4$-alkyl)aminocarbonyl, N-[($C_1$–$C_4$-alkoxy)carbonyl-$C_1$–$C_4$-alkyl]-N-($C_1$–$C_4$-alkyl)aminocarbonyl and di($C_1$–$C_4$-alkyl)aminocarbonyl-($C_1$–$C_4$-alkoxy)carbonyl-$C_1$–$C_4$-alkoxy are: methyl, ethyl, N-propyl, 1-methylethyl, N-butyl, 1-methylpropyl, 2-methylpropyl or 1,1-dimethylethyl;

$C_1$–$C_4$-haloalkyl and the haloalkyl moieties of aminocarbonyl-$C_1$–$C_4$-haloalkyl and $C_1$–$C_4$-alkylaminocarbonyl-$C_1$–$C_4$-haloalkyl are: a $C_1$–$C_4$-alkyl radical as mentioned above, which is partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

the haloalkyl moieties of ($C_1$–$C_4$-alkoxy)carbonyl-$C_2$–$C_4$-haloalkyl and di($C_1$–$C_4$-alkyl)aminocarbonyl-$C_2$–$C_4$-haloalkyl are: ethyl, n-propyl, 1-methylethyl, n-butyl, 1-methylpropyl, 2-methylpropyl or 1,1-dimethylethyl, each of which is partially or fully substituted by fluorine, chlorine, bromine and/or iodine, eg. 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_4$-alkoxy and the alkoxy moieties of $C_1$–$C_4$-alkoxy-$C_1$–$C_4$-alkyl, $C_1$–$C_4$-alkoxy-$C_1$–$C_4$-alkoxy, $C_1$–$C_4$-alkylthio-$C_1$–$C_4$-alkoxy, ($C_1$–$C_4$-alkoxy)carbonyl, ($C_1$–$C_4$-alkoxy)carbonyl-$C_1$–$C_4$-alkyl, ($C_1$–$C_4$-alkoxy)carbonyl-$C_2$–$C_4$-alkenyl, ($C_1$–$C_4$-alkoxy)carbonyl-$C_2$–$C_4$-alkynyl, ($C_1$–$C_4$-alkoxy)carbonyl-$C_2$–$C_4$-haloalkyl, ($C_1$–$C_4$-alkoxy)carbonyl-$C_2$–$C_4$-haloalkenyl, [($C_1$–$C_4$-alkoxy)carbonyl-$C_1$–$C_4$-alkyl]aminocarbonyl-$C_2$–$C_4$-alkenyl, N-[($C_1$–$C_4$-alkoxy)carbonyl-$C_1$–$C_4$-alkyl]-N-($C_1$–$C_4$-alkyl)aminocarbonyl-$C_2$–$C_4$-alkenyl, [($C_1$–$C_4$-alkoxy)carbonyl-$C_1$–$C_4$-alkyl]aminocarbonyl-$C_2$–$C_4$-haloalkenyl, N-[($C_1$–$C_4$-alkoxy)carbonyl-$C_1$–$C_4$-alkyl]-N-($C_1$–$C_4$-alkyl)aminocarbonyl-$C_2$–$C_4$-haloalkenyl, 2-[($C_1$–$C_4$-alkoxy)carbonyl]-pyrrolidin-1-ylcarbonyl-$C_2$–$C_4$-alkenyl, 2-[($C_1$–$C_4$-alkoxy)carbonyl]-pyrrolidin-1-ylcarbonyl-$C_2$–$C_4$-haloalkenyl, ($C_1$–$C_4$-alkoxy)carbonyl-$C_1$–$C_4$-alkoxy, $C_1$–$C_4$-alkoxy-($C_1$–$C_4$-alkoxy)carbonyl-$C_1$–$C_4$-alkoxy, ($C_1$–$C_4$-alkoxy)carbonyl-($C_1$–$C_4$-alkoxy)carbonyl-$C_1$–$C_4$-alkoxy, $C_1$–$C_4$-alkoxyimino-$C_1$–$C_4$-alkyl, 1,1-di($C_1$–$C_4$-alkoxy)-$C_1$–$C_4$-alkyl, $C_1$–$C_4$-alkylaminocarbonyl-$C_1$–$C_4$-alkoxy, di($C_1$–$C_4$-alkyl)aminocarbonyl-$C_1$–$C_4$-alkoxy, [($C_1$–$C_4$-alkoxy)carbonyl-$C_1$–$C_4$-alkyl]aminocarbonyl-$C_1$–$C_4$-alkoxy, N-[($C_1$–$C_4$-alkoxy)carbonyl-$C_1$–$C_4$-alkyl]-N-($C_1$–$C_4$-alkyl)aminocarbonyl-$C_1$–$C_4$-alkoxy, [2-[($C_1$–$C_4$-alkoxy)carbonyl]-pyrrolidin-1-yl]carbonyl-$C_1$–$C_4$-alkoxy, $C_1$–$C_4$-alkoxy-($C_1$–$C_4$-alkoxy)carbonyl, ($C_1$–$C_4$-alkoxy)carbonyl-$C_1$–$C_4$-alkylaminocarbonyl, N-[($C_1$–$C_4$-alkoxy)carbonyl-$C_1$–$C_4$-alkyl]-N-($C_1$–$C_4$-alkyl)aminocarbonyl, 2-[($C_1$–$C_4$-alkoxy)carbonyl]-pyrrolidin-1-ylcarbonyl, aminocarbonyl-($C_1$–$C_4$-alkoxy)carbonyl-$C_1$–$C_4$-alkoxy, ($C_1$–$C_4$-alkyl)aminocarbonyl-($C_1$–$C_4$-alkoxy)carbonyl-$C_1$–$C_4$-alkoxy, di($C_1$–$C_4$-alkyl) aminocarbonyl-($C_1$–$C_4$-alkoxy)carbonyl-$C_1$–$C_4$-alkoxy, 1-pyrrolidinyl-carbonyl-($C_1$–$C_4$-alkoxy)carbonyl-$C_1$–$C_4$-alkoxy, 1-piperidinylcarbonyl-($C_1$–$C_4$-alkoxy)carbonyl-$C_1$–$C_4$-alkoxy, 4-morpholinylcarbonyl-($C_1$–$C_4$-alkoxy)carbonyl-$C_1$–$C_4$-alkoxy are: (methoxy, ethoxy, n-propoxy, 1-methylethoxy, n-butoxy, 1-methylpropoxy, 2-methylpropoxy or 1,1-dimethylethoxy;

$C_1$–$C_4$-haloalkoxy is: $C_1$–$C_4$-alkoxy as mentioned above which is partially or fully substituted by fluorine, chlorine, bromine and/or iodine, eg. difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3- pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

cyano-$C_1$–$C_4$-alkoxy is: cyanomethoxy, 1-cyanoeth-1-yloxy, 2-cyanoeth-1-yloxy, 1-cyanoprop-1-yloxy, 2-cyanoprop-1-yloxy, 3-cyanoprop-1-yloxy, 1-cyanoprop-2-yloxy, 2-cyanoprop-2-yloxy, 1-cyanobut-1-yloxy, 2-cyanobut-1-yloxy, 3-cyanobut-1-yloxy, 4-cyanobut-1-yloxy, 1-cyanobut-2-yloxy, 2-cyano-but-2-yloxy, 1-cyanobut-3-yloxy, 2-cyanobut-3-yloxy, 1-cyano-2-methylprop-3-yloxy, 2-cyano-2-methylprop-3-yloxy, 3-cyano-2-methylprop-3-yloxy or 2-cyano-methylprop-2-yloxy;

$C_1$–$C_4$-alkylthio and the alkylthio moieties of 1,1-di-($C_1$–$C_4$-alkylthio)-$C_1$–$C_4$-alkyl and $C_1$–$C_4$-alkylthio-$C_1$–$C_4$-alkoxy are: methylthio, ethylthio, n-propylthio, 1-methylethylthio, n-butylthio, 1-methylpropylthio, 2-methylpropylthio or 1,1-dimethylethylthio;

$C_1$–$C_4$-haloalkylthio is: $C_1$–$C_4$-alkylthio as mentioned above which is partially or fully substituted by fluorine, chlorine, bromine and/or iodine, eg. difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2,-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

$C_1$–$C_4$-alkylamino and the alkylamino moieties of $C_1$–$C_4$-alkylaminocarbonyl, $C_1$–$C_4$-alkylaminocarbonyl-$C_1$–$C_4$-haloalkyl, $C_1$–$C_4$-alkylaminocarbonyl-$C_2$–$C_4$-haloalkenyl, $C_1$–$C_4$-alkylaminocarbonyl-$C_1$–$C_4$-alkoxy, ($C_1$–$C_4$-alkoxy)carbonyl-$C_1$–$C_4$-alkylaminocarbonyl and ($C_1$–$C_4$-alkyl)aminocarbonyl-($C_1$–$C_4$-alkoxy)carbonyl-$C_1$–$C_4$-alkoxy are: methylamino, ethylamino, n-propylamino, 1-methylethylamino, n-butylamino, 1-methyl-propylamino, 2-methylpropylamino or 1,1-dimethylethylamino;

di($C_1$–$C_4$-alkyl)amino and the dialkylamino moieties of di($C_1$–$C_4$-alkyl)aminocarbonyl, di($C_1$–$C_4$-alkyl)aminocarbonyl-$C_1$–$C_4$-alkyl, di($C_1$–$C_4$-alkyl)aminocarbonyl-$C_2$–$C_4$-alkenyl, di($C_1$–$C_4$-alkyl)aminocarbonyl-$C_2$–$C_4$-alkynyl, di($C_1$–$C_4$-alkyl)aminocarbonyl-$C_2$–$C_4$-haloalkyl, di($C_1$–$C_4$-alkyl)aminocarbonyl-$C_2$–$C_4$-haloalkenyl and di($C_1$–$C_4$-alkyl)aminocarbonyl-$C_1$–$C_4$-alkoxy are: eg. N,N-dimethylamino, N,N-diethylamino, N,N-diisopropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl) amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl) amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1,-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethyl-ethyl)-N-(2-methylpropyl)amino;

$C_1$–$C_4$-alkylsulfinyl is: methylsulfinyl, ethylsulfinyl, n-propylsulfinyl, 1-methylethylsulfinyl, n-butylsulfinyl, 1-methyl-propylsulfinyl, 2-methylpropylsulfinyl or 1,1-dimethylethylsulfinyl;

$C_1$–$C_4$-haloalkylsulfinyl is: $C_1$–$C_4$-alkylsulfinyl as mentioned above which is partially or fully substituted by fluorine, chlorine, bromine and/or iodine, eg. difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2,-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2,-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl or nonafluorobutylsulfinyl;

$C_1$–$C_4$-alkylsulfonyl and the alkylsulfonyl moieties of $C_1$–$C_4$-alkylsulfonylamino and di($C_1$–$C_4$-alkylsulfonyl) amino are: methylsulfonyl, ethylsulfonyl, n-propylisulfonyl, 1-methylethylsulfonyl, n-butylsulfonyl, 1-methylpropylsulfonyl, 2-methylpropylsulfonyl or 1,1-dimethylethylsulfonyl;

$C_1$–$C_4$-haloalkylsulfonyl and the haloalkylsulfonyl moiety of $C_1$–$C_4$-haloalkylsulfonylamino are: $C_1$–$C_4$-alkylsulfonyl as mentioned above which is partially or fully substituted by fluorine, chlorine, bromine and/or iodine, for example, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2,-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2,-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl;

$C_1$–$C_4$-hydroxyalkyl is: hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxyprop-2-yl, 2-hydroxyprop-2-yl, 1-hydroxybut-1-yl, 2-hydroxybut-1-yl, 3-hydroxybut-1-yl, 4-hydroxybut-1-yl, 1-hydroxybut-2-yl, 2-hydroxy-but-2-yl, 1-hydroxybut-3-yl, 2-hydroxybut-3-yl, 1-hydroxy-2-methylprop-3-yl, 2-hydroxy-2-methylprop-3-yl, 3-hydroxy-2-methylprop-3-yl or 2-hydroxy-methylprop-2-yl;

hydroxyimino-$C_1$–$C_4$-alkyl is: hydroxyiminomethyl, 1-(hydroxyimino)eth-1-yl, 2-(hydroxyimino)eth-1-yl, 1-(hydroxyimino)prop-1-yl, 2-(hydroxyimino)prop-1-yl, 3-(hydroxyimino)prop-1-yl, 1-(hydroxyimino)prop-2-yl, 2-(hydroxyimino)prop-2-yl, 1-(hydroxyimino)but-1-yl, 2-(hydroxyimino)but-1-yl, 3-(hydroxyimino)but-1-yl, 4-(hydroxyimino)but-1-yl, 1-(hydroxyimino)but-2-yl, 2-(hydroxyimino)but-2-yl, 1-(hydroxyimino)but-3-yl, 2-(hydroxyimino)but-3-yl, 1-(hydroxyimino)-2-methylprop-3-yl, 2-(hydroxyimino)-2-methylprop-3-yl, 3-(hydroxyimino)-2-methylprop-3-yl or 2-(hydroxyimino)-methylprop-2-yl;

the hydroxycarbonyl-$C_1$–$C_4$-alkyl moieties of hydroxycarbonyl-$C_1$–$C_4$-alkylaminocarbonyl and N-(hydroxycarbonyl-$C_1$–$C_4$-alkyl)-N-($C_1$–$C_4$-alkyl) aminocarbonyl are: hydroxycarbonylmethyl, 1-(hydroxycarbonyl)eth-1-yl, 2-(hydroxycarbonyl)eth-1-yl, 1-(hydroxycarbonyl)prop-1-yl, 2-(hydroxycarbonyl)prop-1-yl, 3-(hydroxycarbonyl)prop-1-yl, 1-(hydroxycarbonyl)prop-2-yl, 2-(hydroxycarbonyl)prop-2-yl, 1-(hydroxycarbonyl)but-1-yl, 2-(hydroxycarbonyl)but-1-yl, 3-(hydroxycarbonyl)but-1-yl, 4-(hydroxycarbonyl)but-1-yl, 1-(hydroxycarbonyl)but-2-yl, 2-(hydroxycarbonyl)but-2-yl, 1-(hydroxycarbonyl)but-3-yl, 2-(hydroxycarbonyl)but-3-yl, 1-(hydroxycarbonyl)-2-methylprop-3-yl, 2-(hydroxycarbonyl)-2-methylprop-3-yl, 3-(hydroxycarbonyl)-2-methylprop-3-yl or 2-(hydroxycarbonyl)-methylprop-2-yl;

$C_3$–$C_6$-cycloalkyl is: cyclopropyl, cyclobutyl, cyclopentyl or cyclohexyl;

$C_3$–$C_6$-cycloalkoxy is: cyclopropyloxy, cyclobutyloxy, cyclopentyloxy or cyclohexyloxy;

$C_3$–$C_6$-cycloalkylamino is: cyclopropylamino, cyclobutylamino, cyclopentylamino or cyclohexylamino;

$C_3$–$C_6$-cycloalkylaminocarbonyl is: cyclopropylaminocarbonyl, cyclobutylaminocarbonyl, cyclopentylaminocarbonyl or cyclohexylaminocarbonyl;

$C_2$–$C_4$-alkenyl and the alkenyl moieties of $C_1$–$C_4$-alkylaminocarbonyl-$C_2$–$C_4$-alkenyl, di($C_1$–$C_4$-alkyl) aminocarbonyl-$C_2$–$C_4$-alkenyl, (hydroxycarbonyl-$C_1$–$C_4$-alkyl)aminocarbonyl-$C_2$–$C_4$-alkenyl, N-(hydroxycarbonyl-$C_1$–$C_4$-alkyl)-N-($C_1$–$C_4$-alkyl) aminocarbonyl-$C_2$–$C_4$-alkenyl, [($C_1$–$C_4$-alkoxy) carbonyl-$C_1$–$C_4$-alkyl]aminocarbonyl-$C_2$–$C_4$-alkenyl, N-[($C_1$–$C_4$-alkoxy)carbonyl-$C_1$–$C_4$-alkyl]-N-($C_1$–$C_4$-alkyl)aminocarbonyl-$C_2$–$C_4$-alkenyl and 2-[($C_1$–$C_4$-alkoxy)carbonyl]-pyrrolidin-1-ylcarbonyl-$C_2$–$C_4$-alkenyl are: vinyl, prop-1-en-1-yl, prop-2-en-1-yl, 1-methylethenyl, n-buten-1-yl, n-buten-2-yl, n-buten-3-yl, 1-methylprop-1-n-1-yl, 2-methylprop-1-en-1-yl, 1-methylprop-2-en-1-yl or 2-methylprop-2-en-1-yl;

the haloalkenyl moieties of ($C_1$–$C_4$-alkoxy)carbonyl-$C_2$–$C_4$-haloalkenyl, aminocarbonyl-$C_2$–$C_4$-haloalkenyl, $C_1$–$C_4$-alkylaminocarbonyl-$C_2$–$C_4$-haloalkenyl, di($C_1$–$C_4$-alkyl)aminocarbonyl-$C_2$–$C_4$-haloalkenyl, (hydroxycarbonyl-$C_1$–$C_4$-alkyl)aminocarbonyl-$C_2$–$C_4$-haloalkenyl, N-(hydroxycarbonyl-$C_1$–$C_4$-alkyl)-N-($C_1$–$C_4$-alkyl)aminocarbonyl-$C_2$–$C_4$-haloalkenyl, [($C_1$–$C_4$-alkoxy)carbonyl-$C_1$–$C_4$-alkyl]-aminocarbonyl-$C_2$–$C_4$-haloalkenyl, N-[($C_1$–$C_4$-alkoxy)carbonyl-$C_1$–$C_4$-alkyl]-N-($C_1$–$C_4$-alkyl)aminocarbonyl-$_2$-$C_4$-haloalkenyl and 2-[($C_1$–$C_4$-alkoxy)carbonyl]-pyrrolidin-1-ylcarbonyl-$C_2$–$C_4$-haloalkenyl are: a $C_2$–$C_4$-alkenyl radical as mentioned above which is partially or fully substituted by fluorine, chlorine, bromine and/or iodine, for example, 2-chloroallyl, 3-chloroallyl or 3,3-dichloroallyl;

$C_{2-4}$-alkynyl and the alkynyl moieties of $C_1$–$C_4$-alkylaminocarbonyl-$C_2$–$C_4$-alkynyl and di($C_1$–$C_4$-alkyl) aminocarbonyl-$C_2$–$C_4$-alkynyl are: ethynyl, prop-1-yn-1-yl, prop-2-yn-1-yl, but-1-yn-1-yl, but-1-yn-3-yl, but-1-yn-4-yl or but-2-yn-1-yl;

$C_2$–$C_4$-alkenyloxy is: vinyloxy, prop-1-en-1-yloxy, prop-2-en-1-yloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy or 2-methylprop-2-en-1-yloxy;

$C_2$–$C_4$-alkynyloxy is: ethynyloxy, prop-1-yn-1-yloxy, prop-2-yn-1-yloxy, but-1-yn-1-yloxy, but-1-yn-3-yloxy, but-1-yn-4-yloxy or but-2-yn-1-yloxy;

hydroxycarbonyl-$C_1$–$C_4$-alkyl and the hydroxycarbonylalkyl moieties of (hydroxycarbonyl-$C_1$–$C_4$-alkyl) aminocarbonyl-$C_2$–$C_4$-alkenyl, (hydroxycarbonyl-$C_1$–$C_4$-alkyl)aminocarbonyl-$C_2$–$C_4$-haloalkenyl, N-(hydroxycarbonyl-$C_1$–$C_4$-alkyl)-N-($C_1$–$C_4$-alkyl) aminocarbonyl-$C_2$–$C_4$-alkenyl and N-(hydroxycarbonyl-$C_1$–$C_4$-alkyl)-N-($C_1$–$C_4$-alkyl)aminocarbonyl-$C_2$–$C_4$-haloalkenyl are: hydroxycarbonylmethyl, 1-(hydroxycarbonyl)eth-1-yl, 2-(hydroxycarbonyl)eth-1-yl, 1-(hydroxycarbonyl)prop-1-yl, 2-(hydroxycarbonyl) prop-1-yl, 3-(hydroxycarbonyl)prop-1-yl, 1-(hydroxycarbonyl)prop-2-yl, 2-(hydroxycarbonyl) prop-2-yl, 1-(hydroxycarbonyl)but-1-yl, 2-(hydroxycarbonyl)but-1-yl, 3-(hydroxycarbonyl)but-1-yl, 4-(hydroxycarbonyl)but-1-yl, 1-(hydroxycarbonyl) but-2-yl, 2-(hydroxycarbonyl)but-2-yl, 1-(hydroxycarbonyl)but-3-yl, 2-(hydroxycarbonyl)but-3-yl, 1-(hydroxycarbonyl)-2-methylprop-3-yl, 2-(hydroxycarbonyl)-2-methylprop-3-yl, 3-(hydroxycarbonyl)-2-methylprop-3-yl, 2-(hydroxycarbonylmethyl)-prop-2-yl;

hydroxycarbonyl-$C_2$–$C_4$-alkenyl is: for example 2-(hydroxycarbonyl)vinyl, 2-(hydroxycarbonyl)allyl, 3-(hydroxycarbonyl)allyl or 4-(hydroxycarbonyl)but-2-yl;

hydroxycarbonyl-$C_2$–$C_4$-alkynyl is: for example 2-hydroxycarbonyl)ethynyl, 3-hydroxycarbonyl-1-propynyl or 3-hydroxycarbonyl-2-propyn-1-yl;

aminocarbonyl-$C_1$–$C_4$-alkyl is: aminocarbonylmethyl, 1-(aminocarbonyl)eth-1-yl, 2-(aminocarbonyl)eth-1-yl, 1-(aminocarbonyl)prop-1-yl, 2-(aminocarbonyl)prop-1-yl, 3-(aminocarbonyl)prop-1-yl, 1-(aminocarbonyl)prop-2-yl, 2-(aminocarbonyl)prop-2-yl, 1-(aminocarbonyl)but-1-yl, 2-(aminocarbonyl)but-1-yl, 3-(aminocarbonyl)but-1-yl, 4-(aminocarbonyl)but-1-yl, 1-(aminocarbonyl)but-2-yl, 2-(aminocarbonyl)but-2-yl, 1-(aminocarbonyl)but-3-yl, 2-(aminocarbonyl)but-3-yl, 1-(aminocarbonyl)-2-methylprop-3-yl, 2-(aminocarbonyl)-2-methylprop-3-yl, 3-(aminocarbonyl)-2-methylprop-3-yl or 2-(aminocarbonylmethyl)-prop-2-yl;

aminocarbonyl-$C_1$–$C_4$-alkoxy is: aminocarbonylmethoxy, 1-(aminocarbonyl)eth-1-yloxy, 2-(aminocarbonyl)eth-1-yloxy, 1-(aminocarbonyl)prop-1-yloxy, 2-(aminocarbonyl)prop-1-yloxy, 3-(aminocarbonyl)prop-1-yloxy, 1-(aminocarbonyl)prop-2-yloxy, 2-(aminocarbonyl)prop-2-yloxy, 1-(aminocarbonyl)but-1-yloxy, 2-(aminocarbonyl)but-1-yloxy, 3-(aminocarbonyl)but-1-yloxy, 4-(aminocarbonyl)but-1-yloxy, 1-(aminocarbonyl)but-2-yloxy, 2-(aminocarbonyl)but-2-yloxy, 1-(aminocarbonyl)but-3-yloxy, 2-(aminocarbonyl)but-3-yloxy, 1-(aminocarbonyl)-2-methylprop-3-yloxy, 2-(aminocarbonyl)-2-methylprop-3-yloxy, 3-(aminocarbonyl)-2-methylprop-3-yloxy or 2-(aminocarbonylmethyl)-prop-2-yloxy;

aminocarbonyl-$C_2$–$C_4$-alkenyl is: for example 2-(aminocarbonyl)vinyl, 2-(aminocarbonyl)allyl, 3-(aminocarbonyl)allyl or 4-(aminocarbonyl)but-2-yl;

aminocarbonyl-$C_{2-4}$-alkynyl is: for example 2-(aminocarbonyl)ethynyl, 3-aminocarbonyl-1-propynyl or 3-aminocarbonyl-2-propyn-1-yl;

($C_1$–$C_4$-alkyl)carbonyl and the alkylcarbonyl moiety of ($C_1$–$C_6$-alkyl)carbonylamino are: methylcarbonyl, ethylcarbonyl, n-propylcarbonyl, 1-methylethylcarbonyl, n-butylcarbonyl, 1-methylpropylcarbonyl, 2-methylpropylcarbonyl or 1,1-dimethylethylcarbonyl;

($C_1$–$C_4$-haloalkyl)carbonyl and the alkylcarbonyl moiety of ($C_1$–$C_6$-alkyl)carbonylamino are: ($C_1$–$C_4$-alkyl)carbonyl as mentioned above which is partially or fully substituted by fluorine, chlorine and/or bromine, for example chloroacetyl, dichloroacetyl, trichloroacetyl, fluoroacetyl, difluoroacetyl, trifluoroacetyl, chlorofluoroacetyl, dichlorofluoroactyl, chlorodifluoroacetyl, 1-fluoropropionyl, 2-fluoropropionyl, 2,2-difluoropropionyl, 3,3,3-trifluoropropionyl, 3-chloro-3-fluoropropionyl, 3-chloro-3,3-difluoropropionyl, 3,3-dichloro-3-fluoropropionyl, trichloropropionyl or pentafluoropropionyl;

hydroxycarbonyl-$C_1$–$C_4$-alkoxy is: hydroxycarbonylmethoxy, 1-(hydroxycarbonyl)eth-1-yloxy, 2-(hydroxycarbonyl)eth-1-yloxy, 1-(hydroxycarbonyl)prop-1-yloxy, 2-(hydroxycarbonyl)-prop-1-yloxy, 3-(hydroxycarbonyl)prop-1-yloxy, 1-(hydroxycarbonyl)prop-2-yloxy, 2-(hydroxcarbonyl)prop-2-yloxy, 1-(hydroxycarbonyl)but-1-yloxy, 2-(hydroxycarbonyl)but-1-yloxy, 3-(hydroxycarbonyl)but-1-yloxy, 4-(hydroxycarbonyl)but-1-yloxy, 1-(hydroxycarbonyl)but-2-yloxy, 2-(hydroxycarbonyl)but-2-yloxy, 1-(hydroxycarbonyl)but-3-yloxy, 2-(hydroxycarbonyl)but-3-yloxy, 1-(hydroxycarbonyl)-2-methylprop-3-yloxy, 2-(hydroxycarbonyl)-2-methylprop-3-yloxy, 3-(hydroxycarbonyl)-2-methylprop-3-yloxy or 2-(hydroxycarbonylmethyl)prop-2-yloxy;

the aminocarbonyl-($C_1$–$C_4$-alkoxy) moiety of aminocarbonyl-($C_1$–$C_4$-alkoxy)carbonyl-$C_1$–$C_4$-alkoxy is: aminocarbonylmethoxy, 1-(aminocarbonyl)eth-1-yloxy, 2-(aminocarbonyl)eth-1-yloxy, 1-(aminocarbonyl)prop-1-yloxy, 2-(aminocarbonyl)prop-1-yloxy, 3-(aminocarbonyl)prop-1-yloxy, 1-(aminocarbonyl)prop-2-yloxy, 2-(aminocarbonyl)prop-2-yloxy, 1-(aminocarbonyl)but-1-yloxy, 2-(aminocarbonyl)but-1-yloxy, 3-(aminocarbonyl)but-1-yloxy, 4-(aminocarbonyl)but-1-yloxy, 1-(aminocarbonyl)but-2-yloxy, 2-(aminocarbonyl)but-2-yloxy, 1-(aminocarbonyl)but-3-yloxy, 2-(aminocarbonyl)but-3-yloxy, 1-(aminocarbonyl)-2-methylprop-3-yloxy, 2-(aminocarbonyl)-2-methylprop-3-yloxy, 3-(aminocarbonyl)-2-methylprop-3-yloxy or 2-(aminocarbonylmethyl)-prop-2-yloxy;

1-pyrrolidinylcarbonyl-$C_1$–$C_4$-alkoxy and the 1-pyrrolidinylcarbonylalkoxy moiety of 1-pyrrolidinylcarbonyl-($C_1$–$C_4$-alkoxy)carbonyl-$C_1$–$C_4$-alkoxy are: 1-pyrrolidinylcarbonylmethoxy, 1-(1-pyrrolidinylcarbonyl)eth-1-yloxy, 2-(1-pyrrolidinylcarbonyl)eth-1-yloxy, 1-(1-pyrrolidinylcarbonyl)prop-1-yloxy, 2-(1-pyrrolidinylcarbonyl)prop-1-yloxy, 3-(1-pyrrolidinylcarbonyl)prop-1-yloxy, 1-(1-pyrrolidinylcarbonyl)prop-2-yloxy, 2-(1-pyrrolidinylcarbonyl)prop-2-yloxy, 1-(1-pyrrolidinylcarbonyl)but-1-yloxy, 2-(1-pyrrolidinylcarbonyl)but-1-yloxy, 3-(1-pyrrolidinylcarbonyl)but-1-yloxy, 4-(1-pyrrolidinylcarbonyl)but-1-yloxy, 1-(1-pyrrolidinylcarbonyl)but-2-yloxy, 2-(1-pyrrolidinylcarbonyl)but-2-yloxy, 1-(1-pyrrolidinylcarbonyl)but-2-yloxy, 2-(1-pyrrolidinylcarbonyl)but-3-yloxy, 1-(1-pyrrolidinylcarbonyl)but-3-yloxy, 1-(1-pyrrolidinylcarbonyl)-2-methylprop-3-yloxy, 2-(1-pyrrolidinylcarbonyl)-2-methylprop-3-yloxy, 3-(1-pyrrolidinylcarbonyl)-2-methylprop-3-yloxy or 2-(1-pyrrolidinylcarbonylmethyl)-prop-2-yloxy;

1-piperidinylcarbonyl-$C_1$–$C_4$-alkoxy and the 1-piperidinylcarbonylalkoxy moiety of 1-piperidinylcarbonyl-($C_1$–$C_4$-alkoxy)carbonyl-$C_1$–$C_4$-alkoxy are: 1-piperidinylcarbonylmethoxy, 1-(1-piperidinylcarbonyl)eth-1-yloxy, 2-(1-piperidinylcarbonyl)eth-1-yloxy, 1-(1-piperidinylcarbonyl)prop-1-yloxy, 2-(1-piperidinylcarbonyl)prop-1-yloxy, 3-(1-piperidinylcarbonyl)prop-1-yloxy, 1-(1-piperidinylcarbonyl)prop-2-yloxy, 2-(1-piperidinylcarbonyl)prop-2-yloxy, 1-(1-piperidinylcarbonyl)but-1-yloxy, 2-(1-piperidinylcarbonyl)but-1-yloxy, 3-(1-piperidinylcarbonyl)but-1-yloxy, 4-(1-piperidinylcarbonyl)but-1-yloxy, 1-(1-piperidinylcarbonyl)but-1-yloxy, 2-(1-piperidinylcarbonyl)but-2-yloxy, 1-(1-piperidinylcarbonyl)but-2-yloxy, 2-(1-piperidinylcarbonyl)but-3-yloxy, 1-(1-piperidinylcarbonyl)but-3-yloxy, 1-(1-piperidinylcarbonyl)-2-methylprop-3-yloxy, 2-(1-piperidinylcarbonyl)-2-methylprop-3-yloxy, 3-(1-piperidinylcarbonyl)-2-methylprop-3-yloxy or 2-(1-piperidinylcarbonylmethyl)-prop-2-yloxy;

4-morpholinylcarbonyl-$C_1$–$C_4$-alkoxy and the 4-morpholinylcarbonylalkoxy moiety of 4-morpholinylcarbonyl-($C_1$–$C_4$-alkoxy)carbonyl-$C_1$–$C_4$-alkoxy are: 4-morpholinylcarbonylmethoxy, 1-(4-morpholinylcarbonyl)eth-1-yloxy, 2-(4-morpholinylcarbonyl)eth-1-yloxy, 1-(4-morpholinylcarbonyl)prop-1-yloxy, 2-(4-morpholinylcarbonyl)prop-1-yloxy, 3-(4-morpholinylcarbonyl)prop-1-yloxy, 1-(4-morpholinylcarbonyl)prop-2-yloxy, 2-(4-morpholinylcarbonyl)prop-2-yloxy, 1-(4-morpholinylcarbonyl)prop-2-yloxy, 2-(4-morpholinylcarbonyl)but-1-yloxy, 3-(4-morpholinylcarbonyl)but-1-yloxy, 4-(4-morpholinylcarbonyl)but-1-yloxy, 1-(4-morpholinylcarbonyl)but-1-yloxy, 2-(4-morpholinylcarbonyl)but-2-yloxy, 1-(4-morpholinylcarbonyl)but-2-yloxy, 2-(4-morpholinylcarbonyl)but-3-yloxy, 1-(4- morpholinylcarbonyl)-2-methylprop-3-yloxy, 2-(4-morpholinylcarbonyl)-2-methylprop-3-yloxy, 3-(4-morpholinylcarbonyl)-2-methylprop-3-yloxy or 2-(4-morpholinylcarbonylmethyl)prop-2-yloxy.

With a view to the use of the compounds of the formula I or I' according to the invention as herbicides and/or as compounds which have a defoliant/desiccant action, the variables preferably have the following meanings, in each case either on their own or in combination:

$R^1$ is hydrogen;
$R^2$ is $C_1$–$C_4$-haloalkyl, in particular trifluoromethyl;
$R^3$ is hydrogen;
$R^4$ is halogen, in particular chlorine;
$R^5$ is hydrogen, fluorine or chlorine;
$R^6$ is hydrogen;
$R^7$, $R^8$, $R^9$, $R^{10}$ are hydrogen, fluorine, chlorine or methyl;
$R^{11}$ has all meanings with the exception of hydrogen, cyano and halogen;
$R^{13}$ is hydrogen.

Particularly preferred compounds Ia are listed in Table 1 below (= I where n=zero; $R^1$, $R^3$, $R^5$ to $R^{10}$, $R^{12}$ and $R^{13}$=hydrogen; $R^2$=trifluoromethyl; $R^4$=chlorine):

TABLE 1

Ia

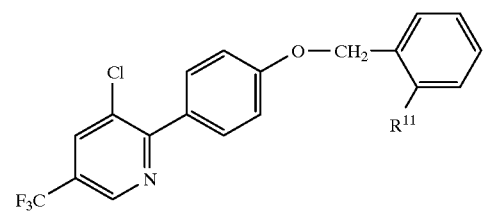

M.p.;
IR data
(ν[cm$^{-1}$]);
$^1$H NMR data
(in CDCl$_3$;
TMS; δ [ppm])

| No. | $R^{11}$ |
|---|---|
| Ia.001 | OH |
| Ia.002 | OCH$_3$ |
| Ia.003 | OC$_2$H$_5$ |
| Ia.004 | OCH$_2$—C$_2$H$_5$ |
| Ia.005 | OCH(CH$_3$)$_2$ |
| Ia.006 | OCH$_2$—CH═CH$_2$ |
| Ia.007 | OCH$_2$—C≡CH |
| Ia.006 | OCH(CH$_3$)—C≡CH |
| Ia.009 | OCH$_2$—CO—OCH$_3$ |
| Ia.010 | OCH$_2$—CO—OC$_2$H$_5$ |
| Ia.011 | OCH$_2$—CO—OCH$_2$—CO—OCH$_3$ |
| Ia.012 | OCH$_2$—CO—OCH$_2$—CO—OC$_2$H$_5$ |
| Ia.013 | OCH$_2$—CO—NH$_2$ |
| Ia.014 | OCH$_2$—CO—NH—CH$_3$ |
| Ia.015 | OCH$_2$—CO—N(CH$_3$)$_2$ |
| Ia.016 | OCH$_2$—CO—OCH$_2$—CO—NH$_2$ |
| Ia.017 | OCH$_2$—CO—OCH$_2$—CO—NH—CH$_3$ |
| Ia.018 | OCH$_2$—CO—OCH$_2$—CO—N(CH$_3$)$_2$ |
| Ia.019 | OCH(CH$_3$)—CO—OCH$_3$ |
| Ia.020 | OCH(CH$_3$)—CO—OC$_2$H$_5$ |
| Ia.021 | OCH(CH$_3$)—CO—OCH$_2$—CO—OCH$_3$ |
| Ia.022 | OCH(CH$_3$)—CO—OCH$_2$—CO—OC$_2$H$_5$ |
| Ia.023 | OCH(CH$_3$)—CO—NH$_2$ |
| Ia.024 | OCH(CH$_3$)—CO—NH—CH$_3$ |
| Ia.025 | OCH(CH$_3$)—CO—N(CH$_3$)$_2$ |
| Ia.026 | OCH(CH$_3$)—CO—OCH$_2$—CO—NH$_2$ |
| Ia.027 | OCH(CH$_3$)—CO—OCH$_2$—CO—NH—CH$_3$ |
| Ia.028 | OCH(CH$_3$)—CO—OCH$_2$—CO—N(CH$_3$)$_2$ |
| Ia.029 | OCH(CH$_3$)—CO—OCH(CH$_3$)—CO—OCH$_3$ |
| Ia.030 | OCH(CH$_3$)—CO—OCH(CH$_3$)—CO—OC$_2$H$_5$ |
| Ia.031 | OCH(CH$_3$)—CO—OCH(CH$_3$)—CO—NH$_2$ |
| Ia.032 | OCH(CH$_3$)—CO—OCH(CH$_3$)—CO—NH—CH$_3$ |
| Ia.033 | OCH(CH$_3$)—CO—OCH(CH$_3$)—CO—N(CH$_3$)$_2$ |
| Ia.034 | OCH$_2$—CO—(pyrrolidin-1-yl) |
| Ia.035 | OCH(CH$_3$)—CO—(pyrrolidin-1-yl) |
| Ia.036 | OCH$_2$—CO—(piperidin-1-yl) |
| Ia.037 | OCH(CH$_3$)—CO—(piperidin-1-yl) |
| Ia.038 | OCH$_2$—CO—(morpholin—4—yl) |
| Ia.039 | OCH(CH$_3$)—CO—(morpholin—4—yl) |
| Ia.040 | OCH$_2$—CO—OCH$_2$—CO—(pyrrolidin-1-yl |
| Ia.041 | OCH(CH$_3$)—CO—OCH$_2$—CO—(pyrrolidin-1-yl) |
| Ia.042 | OCH$_2$—CO—OCH$_2$—CO—(piperidin-1-yl) |
| Ia.043 | OCH(CH$_3$)—CO—OCH$_2$—CO—(piperidin-1-yl) |
| Ia.044 | OCH$_2$—CO—OCH$_2$—CO—(morpholin—4—yl) |
| Ia.045 | OCH(CH$_3$)—CO—OCH$_2$—CO—(morpholin—4—yl) |

TABLE 1-continued

Ia

[Structure: pyridine with Cl, CF3 substituents, connected to phenyl-O-CH2-phenyl(R11)]

| No. | R11 | M.p.; IR data (ν[cm⁻¹]); ¹H NMR data (in CDCl₃; TMS; δ [ppm]) |
|---|---|---|
| Ia.046 | OCH₂—CO—NH—CH₂—CO—OCH₃ | |
| Ia.047 | OCH(CH₃)—CO—NH—CH₂—CO—OCH₃ | |
| Ia.048 | OCH₂—CO—NH—CH₂—CO—OC₂H₅ | |
| Ia.049 | OCH(CH₃)—CO—NH—CH₂—CO—OC₂H₅ | |
| Ia.050 | OCH₂—CO—N(CH₃)—CH₂—CO—OCH₃ | |
| Ia.051 | OCH(CH₃)—CO—N(CH₃)—CH₂—CO—OCH₃ | |
| Ia.052 | OCH₂—CO—N(CH₃)—CH₂—CO—OC₂H₅ | |
| Ia.053 | OCH(CH₃)—CO—N(CH₃)—CH₂—CO—OC₂H₅ | |
| Ia.054 | OCH₂—CO—N(pyrrolidine-2-COOCH₃) | |
| Ia.055 | OCH(CH₃)—CO—N(pyrrolidine-2-COOCH₃) | |
| Ia.056 | OCH₂—CO—N(pyrrolidine-2-COOC₂H₅) | |
| Ia.057 | OCH(CH₃)—CO—N(pyrrolidine-2-COOC₂H₅) | |
| Ia.058 | OCH₂—CO—NH—CH(CH₃)—CO—OCH₃ | |
| Ia.059 | OCH(CH₃)—CO—NH—CH(CH₃)—CO—OCH₃ | |
| Ia.060 | OCH₂—CO—NH—CH(CH₃)—CO—OC₂H₅ | |
| Ia.061 | OCH(CH₃)—CO—NH—CH(CH₃)—CO—OC₂H₅ | |
| Ia.062 | OCH₂—CO—N(CH₃)—CH(CH₃)—CO—OCH₃ | |
| Ia.063 | OCH(CH₃)—CO—N(CH₃)—CH(CH₃)—CO—OCH₃ | |
| Ia.064 | OCH₂—CO—N(CH₃)—CH(CH₃)—CO—OC₂H₅ | |
| Ia.065 | OCH(CH₃)—CO—N(CH₃)—CH(CH₃)—CO—OC₂H₅ | |
| Ia.066 | cyclopentyloxy | |
| Ia.067 | cyclohexyloxy | |
| Ia.068 | OCH₂—CH₂—CO—OCH₃ | |
| Ia.069 | OCH₂—CH₂—CO—OC₂H₅ | |
| Ia.070 | OCH₂—CH₂CH₂—CO—OCH₃ | |
| Ia.071 | C≡N | |
| Ia.072 | CO—OH | |
| Ia.073 | CO—O⁻Na⁺ | |
| Ia.074 | CO—O⁻K⁺ | |
| Ia.075 | CO—OCH₃ | 64–65° C. |
| Ia.076 | CO—OC₂H₅ | 86–87° C. |
| Ia.077 | CO—OCH₂—C₂H₅ | |
| Ia.078 | CO—OCH(CH₃)₂ | |
| Ia.079 | CO—OCH₂—CH₂—C₂H₅ | |
| Ia.080 | CO—OCH₂—CH₂CH₂—C₂H₅ | |
| Ia.081 | CO—OCH₂—CO—OCH₃ | |

TABLE 1-continued

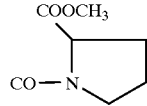

Ia

| No. | R[11] | M.p.; IR data ($\nu$[cm$^{-1}$]); $^1$H NMR data (in CDCl$_3$; TMS; $\delta$ [ppm]) |
|---|---|---|
| Ia.082 | CO—OCH$_2$—CO—OC$_2$H$_5$ | |
| Ia.083 | CO—OCH(CH$_3$)—CO—OCH$_3$ | |
| Ia.084 | CO—OCH(CH$_3$)—CO—OC$_2$H$_5$ | |
| Ia.085 | CO—OCH$_2$—CH$_2$—OCH$_3$ | |
| Ia.086 | CO—OCH$_2$—CH$_2$—OC$_2$H$_5$ | |
| Ia.087 | CO—NH$_2$ | |
| Ia.088 | CO—NH—CH$_3$ | |
| Ia.089 | CO—N(CH$_3$)$_2$ | |
| Ia.090 | CO—N(C$_2$H$_5$)$_2$ | |
| Ia.091 | CO-(pyrrolidin-1-yl) | |
| Ia.092 | CO-(piperidin-1-yl) | |
| Ia.093 | CO-(morpholin-4-yl) | |
| Ia.094 | CO—NH—CH$_2$—CO—OCH$_3$ | |
| Ia.095 | CO—NH—CH$_2$—CO—OC$_2$H$_5$ | |
| Ia.096 | CO—N(CH$_3$)—CH$_2$—CO—OCH$_3$ | |
| Ia.097 | CO—N(CH$_3$)—CH$_2$—CO—OC$_2$H$_5$ | |
| Ia.098 | CO—NH—CH(CH$_3$)—CO—OCH$_3$ | |
| Ia.099 | CO—NH—CH(CH$_3$)—CO—OC$_2$H$_5$ | |
| Ia.100 | CO—N(CH$_3$)—CH(CH$_3$)—CO—OCH$_3$ | |
| Ia.101 | CO—N(CH$_3$)—CH(CH$_3$)—CO—OC$_2$H$_5$ | |
| Ia.102 | 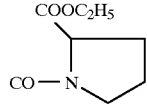 | |
| Ia.103 | 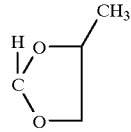 | |
| Ia.104 | CO—OCH$_2$—CO—NH$_2$ | |
| Ia.105 | CO—OCH$_2$—CO—NH—CH$_3$ | |
| Ia.106 | CO—OCH$_2$—CO—N(CH$_3$)$_2$ | |
| Ia.107 | CO—OCH(CH$_3$)—CO—NH$_2$ | |
| Ia.108 | CO—OCH(CH$_3$)—CO—NH—CH$_3$ | |
| Ia.109 | CO—OCH(CH$_3$)—CO—N(CH$_3$)$_2$ | |
| Ia.110 | CO—OCH$_2$—CO(pyrrolidin-1-yl) | |
| Ia.111 | CO—OCH$_2$—CO-(piperidin-1-yl) | |
| Ia.112 | CO—OCH$_2$—CO-(morpholin-4-yl) | |
| Ia.113 | CHO | |
| Ia.114 | CO—CH$_3$ | |
| Ia.115 | CO—CCl$_3$ | |
| Ia.116 | CH(OCH$_3$)$_2$ | |
| Ia.117 | CH(OC$_2$H$_5$)$_2$ | |
| Ia.118 | 1,3-dioxolan-2-yl | |
| Ia.119 |  | |

TABLE 1-continued

[Structure Ia: 3-chloro-5-(trifluoromethyl)-2-[4-(benzyloxy)phenyl]pyridine with R¹¹ substituent on benzyl ring]

Ia

| No. | R¹¹ | M.p.; IR data ($\nu$[cm$^{-1}$]); $^1$H NMR data (in CDCl$_3$; TMS; $\delta$ [ppm]) |
|---|---|---|
| Ia.120 | [structure: -CH(O-)(O-CH2-) with COOCH3] | |
| Ia.121 | 1,3-dioxan-2-yl | |
| Ia.122 | 5-methyl-1,3-dioxan-2-yl | |
| Ia.123 | 5,5-dimethyl-1,3-dioxan-2-yl | |
| Ia.124 | 1,3-dithiolan-2-yl | |
| Ia.125 | [structure: -CH(S-)(S-CH2-) with CH3] | |
| Ia.126 | 1,3-dithian-2-yl | |
| Ia.127 | CH=N—OH | |
| Ia.128 | CH=N—OCH$_3$ | |
| Ia.129 | CH=N—OC$_2$H$_5$ | |
| Ia.130 | CH=N—OCH$_2$—C$_2$H$_5$ | |
| Ia.131 | CH=N—OCH$_2$—CO—OCH$_3$ | |
| Ia.132 | CH=N—OCH$_2$—CO—OC$_2$H$_5$ | |
| Ia.133 | NO$_2$ | |
| Ia.134 | NH—OH | |
| Ia.135 | NH$_2$ | |
| Ia.136 | N(SO$_2$CH$_3$)$_2$ | |
| Ia.137 | NH—SO$_2$—CH$_3$ | |
| Ia.138 | N(SO$_2$—C$_2$H$_5$)$_2$ | |
| Ia.139 | NH—SO$_2$—C$_2$H$_5$ | |
| Ia.140 | NH—SO$_2$—CH$_2$—C$_2$H$_5$ | |
| Ia.141 | H | |
| Ia.142 | F | |
| Ia.143 | Cl | |
| Ia.144 | Br | |
| Ia.145 | I | |
| Ia.146 | CH$_3$ | |
| Ia.147 | CH$_2$Cl | |
| Ia.148 | CH$_2$Br | |
| Ia.149 | CCl$_3$ | |
| Ia.150 | CHBr$_2$ | |
| Ia.151 | CH=CH—CO—OCH$_3$ | |
| Ia.152 | CH=CH—CO—OC$_2$H$_5$ | |
| Ia.153 | CH=CH—CO—OCH$_2$—C$_2$H$_5$ | |
| Ia.154 | CH=C(CH$_3$)—CO—OCH$_3$ | |
| Ia.155 | CH=C(CH$_3$)—CO—OC$_2$H$_5$ | |
| Ia.156 | CH=C(CH$_3$)—CO—OCH$_2$—C$_2$H$_5$ | |
| Ia.157 | CH=C(Cl)—CO—OCH$_3$ | |
| Ia.158 | CH=C(Cl)—CO—OC$_2$H$_5$ | |
| Ia.159 | CH=C(Cl)—CO—OCH$_2$—C$_2$H$_5$ | |
| Ia.160 | CH=CH—COOH | |
| Ia.161 | CH=C(CH$_3$)—COOH | |
| Ia.162 | CH=C(Cl)—COOH | |
| Ia.163 | CH=CH—CO—Cl | |
| Ia.164 | CH=C(Cl)—CO—Cl | |

TABLE 1-continued

Ia

[Structure: 3-chloro-5-trifluoromethyl-2-phenylpyridine with para-O-CH₂-phenyl(R¹¹) substituent]

| No. | R¹¹ | M.p.; IR data (ν[cm⁻¹]); ¹H NMR data (in CDCl₃; TMS; δ [ppm]) |
|---|---|---|
| Ia.165 | CH=C(CH₃)—CO—Cl | |
| Ia.166 | CH=CH—CO—NH₂ | |
| Ia.167 | CH=C(Cl)—CO—NH₂ | |
| Ia.168 | CH=C(CH₃)—CO—NH₂ | |
| Ia.169 | CH=CH—CO—NH—CH₃ | |
| Ia.170 | CH=C(Cl)—CO—NH—CH₃ | |
| Ia.171 | CH=C(CH₃)—CO—NH—CH₃ | |
| Ia.172 | CH=CH—CO—N(CH₃)₂ | |
| Ia.173 | CH=C(Cl)—CO—N(CH₃)₂ | |
| Ia.174 | CH=C(CH₃)—CO—N(CH₃)₂ | |
| Ia.175 | CH=CH—CO—NH—CH₂—CO—OCH₃ | |
| Ia.176 | CH=C(Cl)—CO—NH—CH₂—CO—OCH₃ | |
| Ia.177 | CH=C(CH₃)—CO—NH—CH₂—CO—OCH₃ | |
| Ia.178 | CH=CH—CO—NH—CH₂—CO—OC₂H₅ | |
| Ia.179 | CH=C(Cl)—CO—NH—CH₂—CO—OC₂H₅ | |
| Ia.180 | CH=C(CH₃)—CO—NH—CH₂—CO—OC₂H₅ | |
| Ia.181 | CH=CH—CO—N(CH₃)—CH₂—CO—OCH₃ | |
| Ia.182 | CH=C(Cl)—CO—N(CH₃)—CH₂—CO—OCH₃ | |
| Ia.183 | CH=C(CH₃)—CO—N(CH₃)—CH₂—CO—OCH₃ | |
| Ia.184 | CH=CH—CO—N(CH₃)—CH₂—CO—OC₂H₅ | |
| Ia.185 | CH=C(Cl)—CO—N(CH₃)—CH₂—CO—OC₂H₅ | |
| Ia.186 | CH=C(CH₃)—CO—N(CH₃)—CH₂—CO—OC₂H₅ | |
| Ia.187 | CH=CH—CO—N(pyrrolidine-2-COOCH₃) | |
| Ia.188 | CH=CH—CO—N(pyrrolidine-2-COOC₂H₅) | |
| Ia.189 | CH=C(Cl)—CO—N(pyrrolidine-2-COOCH₃) | |
| Ia.190 | CH₂—CH(Cl)—CO—OCH₃ | |
| Ia.191 | CH₂—CH(Cl)—CO—OC₂H₅ | |
| Ia.192 | CH₂—CH(CH₃)—CO—OCH₃ | |
| Ia.193 | CH₂—CH(CH₃)—CO—OC₂H₅ | |
| Ia.194 | CH₂—CH₂—CO—OCH₃ | |
| Ia.195 | CH₂—CH₂—CO—OC₂H₅ | |
| Ia.196 | OCH₂—CH₂CH₂—CO—OC₂H₅ | |
| Ia.197 | OCH₂—CN | |
| Ia.198 | OCH₂—CH₂—CN | |
| Ia.199 | OCH(CH₃)—CN | |
| Ia.200 | OCH₂—CH₂CH₂—CN | |
| Ia.201 | OCH(CH₃)—COOH | |

Other particularly preferred substituted 2-phenylpyridines of the formula I are those which follow: the compounds Ib.001–Ib.201, which only differ from the corresponding compounds Ia.001–Ia.201 by the fact that $R^5$ is fluorine:

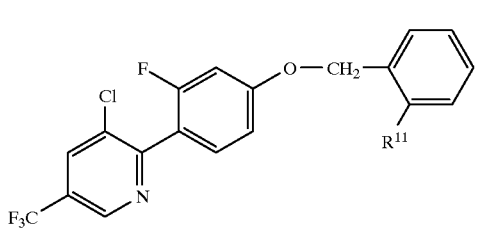
Ib the compounds Ic.001–Ic.201, which only differ from the corresponding compounds Ia.001–Ia.201 by the fact that $R^9$ is methyl:

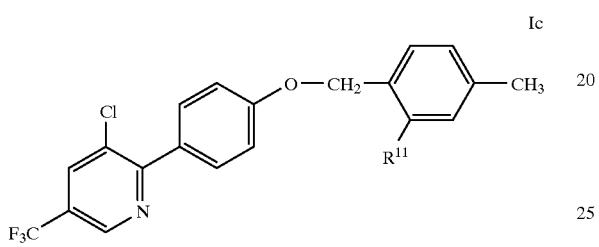
Ic the compounds Id.001–Id.201, which only differ from the corresponding compounds Ia.001–Ia.201 by the fact that $R^5$ is fluorine and $R^9$ is methyl:

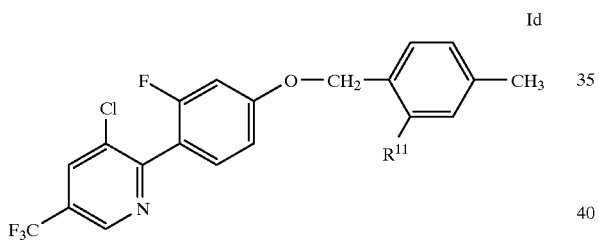
Id the compounds Ie.001–Ie.201, which only differ from the corresponding compounds Ia.001–Ia.201 by the fact that $R^9$ is chlorine:

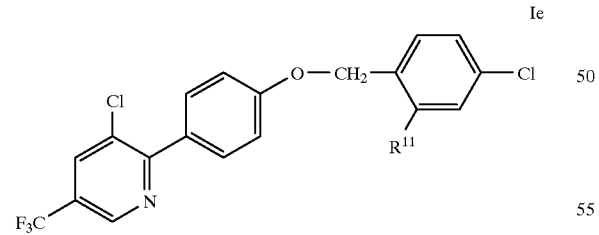
Ie the compounds If.001–If.201, which only differ from the corresponding compounds Ia.001–Ia.201 by the fact that $R^5$ is fluorine and $R^9$ is chlorine:

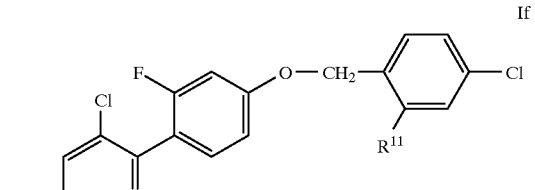
If the compounds Ig.001–Ig.201, which only differ from the corresponding compounds Ia.001–Ia.201 by the fact that $R^{10}$ is methyl:

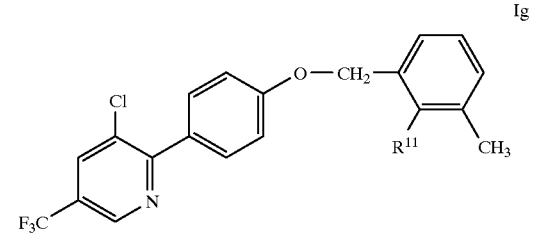
Ig the compounds Ih.001–Ih.201, which only differ from the corresponding compounds Ia.001–Ia.201 by the fact that $R^5$ is fluorine and $R^{10}$ is methyl:

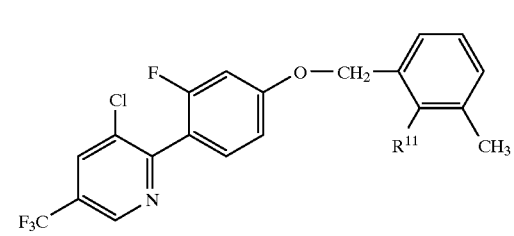
Ih the compounds Ii.001–Ii.201, which only differ from the corresponding compounds Ia.001–Ia.201 by the fact that $R^{10}$ is chlorine:

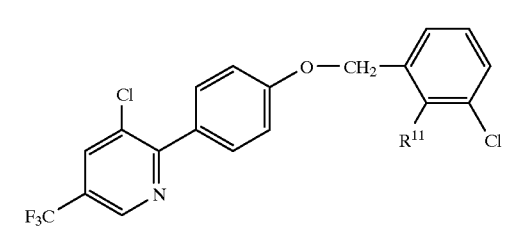
Ii the compounds Ik.001–Ik.201, which only differ from the corresponding compounds Ia.001–Ia.201 by the fact that $R^5$ is fluorine and $R^{10}$ is chlorine:

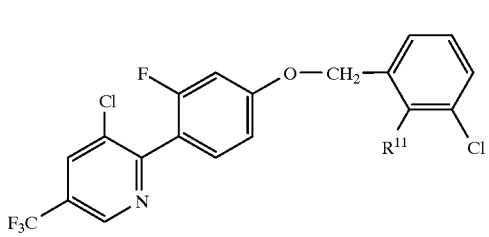

The substituted 2-phenylpyridines of the formula I can be obtained via various routes, for example by one of the following processes:

Process A:

Reaction of 2-(4-hydroxyphenyl)pyridines II with benzyl halides or benzyl mesylates III in a manner known per se {see, for example, H. Meerwein in Houben-Weyl, Methoden der organischen Chemie, Vol. VI/3, Part 3, page 54 et seq., and A. D. Batcho & W. Leingruber, Org. Synth. 63, (1984) 214}:

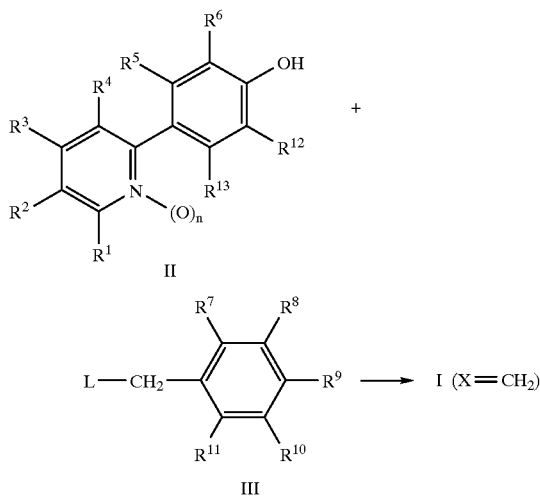

L is chlorine, bromine or methylsulfonyloxy.

The reaction is preferably carried out in an inert aprotic solvent such as dimethylformamide, dimethyl sulfoxide, acetonitrile and acetone.

Depending on the respective substituents and the reaction conditions, it may be advantageous to carry out the process in the presence of an approximately equivalent amount of base, based on II.

Examples of suitable bases are alkali metal carbonates, such as sodium hydrogen carbonate and sodium carbonate, furthermore nitrogen bases, such as pyridine and triethylamine.

The reaction temperature is normally from 0 to 100° C.

As a rule, the components are employed in approximately stoichiometric ratio, but an excess of one of the components, for example with a view to as complete a reaction as possible of the other component, may be advantageous.

Process B:

Reaction of 2-(4-hydroxyphenyl)pyridines II with benzoyl halides IV in a manner known per se (see, for example, H. Henecka in Houben-Weyl, Methoden der organischen Chemie, Vol. VIII, page 543 et seq., and T. S. Wheeler, Org. Synth. Coll. Vol. IV 1963, page 478):

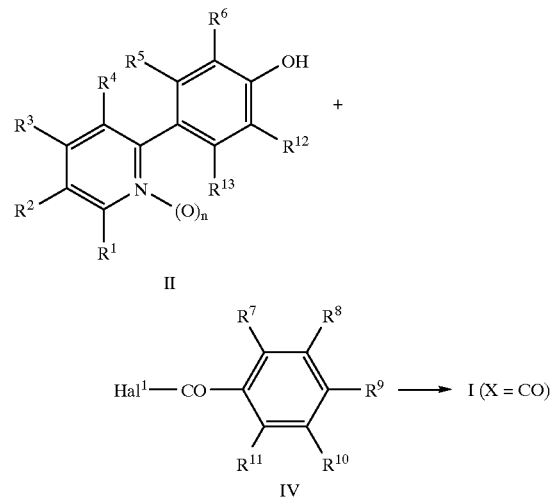

$Hal^1$ is chlorine or bromine.

Suitable inert solvents are, in particular, chlorinated aliphatic hydrocarbons, such as chloroform, dichloromethane, carbon tetrachloride and 1,2-dichloroethane.

Depending on the respective substituents and the reaction conditions, it may be advantageous to carry out the process in the presence of a base.

As regards base, reaction temperature and the ratios of amounts, the information given for process A) applies here too.

Process C:

Reaction of 2-(4-hydroxyphenyl)pyridines II with substituted phthalic anhydrides V in a manner known per se {see, for example, H. Henecka in Houben-Weyl, Methoden der organischen Chemie, Vol. VIII, page 547 et seq. and P. C. Crofts et al., Org. Prep. Proced. Int. 22(4), (1990) 538–540}:

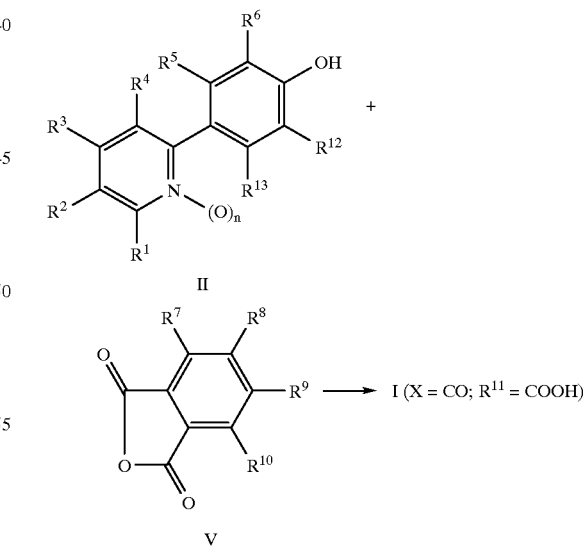

Examples of suitable solvents are the chlorohydrocarbons mentioned for process B.

The reaction is normally carried out at from 0 to 100° C.

As a rule, the reactants are employed in approximately stoichiometric ratios, but it is also possible to employ an excess of one of the components.

Process D:

Oxidation of substituted 2-phenylpyridines of the formula I where n is zero in a manner known per se {cf., for example, A. Albini and S. Pietra, Heterocyclic N-Oxides, CRC-Press Inc., Boca Raton, USA 1991; H. S. Mosher et al., Org. Synth. Coll. Vol. IV 1963, 828; E. C. Taylor et al., Org. Synth. Coll. Vol. IV 1963, 704; T. W. Bell et. al., Org. Synth. 69, (1990) 226}:

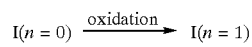

Amongst the oxidants customary for oxidizing the pyridine ring, mention may be made, for example, of peracetic acid, pertrifluoroacetic acid, perbenzoic acid, m-chloroperbenzoic acid, monopermaleic acid, magnesium monoperphthalate, sodium perborate, Oxone® (contains peroxydisulfate), pertungstic acid and hydrogen peroxide.

Examples of suitable solvents are water, sulfuric acid, carboxylic acids, such as acetic and trifluoroacetic acid, and halogenated hydrocarbons, such as dichloromethane and chloroform.

As a rule, the oxidation is successfully carried out at from 0° C. to the boiling point of the reaction mixture.

As a rule, the oxidant is employed in at least equimolar amounts based on the starting compound. In individual cases, a large excess of oxidant may also be advantageous.

Process E:

Reaction of 2-halopyridines VI with boronic acids VII, boroxines VIII or, if the substituents $R^1$ to $R^{13}$ are inert under the conditions of a Grignard reaction, with Grignard compounds IX in a manner known per se in the presence of a base and of a catalyst (cf., for example, DE-A 43 23 916 and the literature cited therein):

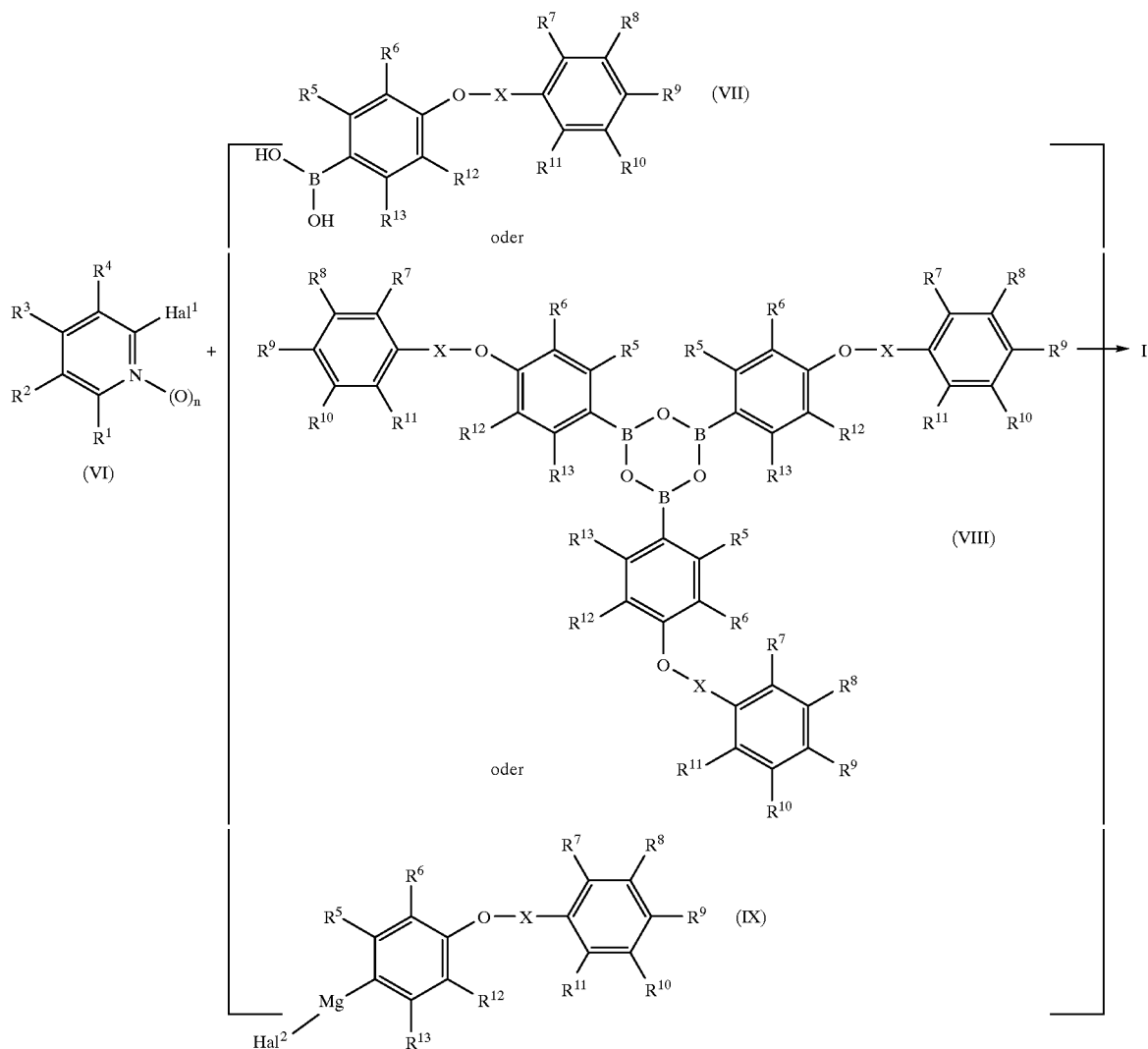

Hal$^1$ is chlorine or bromine;
Hal$^2$ is bromine or iodine.

As a rule, the process is carried out in an inert solvent (mixture), for example in tetrahydrofuran/water, dioxane/water, dimethoxyethane/water, toluene/water, or in dimethylformamide.

Suitable catalysts are palladium and nickel compounds, such as tetrakis(triphenylphosphine)palladium(0), [1,2-bis(diphenylphosphino)ethane]palladium(II) chloride, [1,1'-bis(diphenylphosphino)ferrocene]palladium(II) chloride, palladium(II) acetate and bis(triphenylphosphine)nickel(II) chloride. They are preferably employed in catalytic amounts.

Examples of suitable bases are alkali metal carbonates, such as sodium carbonate, alkali metal hydrogen carbonates, such as sodium hydrogen carbonate, alkali metal hydroxides, such as sodium hydroxide, alkali metal phosphates, such as potassium phosphate, and alkylamines, such as triethylamine.

The reaction is generally carried out from 20° C. to the boiling point of the reaction mixture.

The molar ratio of VI to base is generally 1:1 to 1:5.

As a rule, the starting compounds VI and VII, VIII or IX are employed in approximately equivalent amounts, but an excess of one of the components may also be employed.

The 2-halopyridines VI are known or can be obtained in a manner known per se (cf., for example, D. Spitzner in Houben-Weyl, Methoden der Organischen Chemie [Methods in Organic Chemistry], Vol. E7b, 286 et seq.). Those boronic acids VII and boroxines VIII which are already known from, for example, DE-A 42 36 105, EP-A 569 193 or JP-A 05/025 158 can be prepared in a manner known per se (cf., for example, M. F. Lappert, Chem. Rev. 56, (1956) 959; K. Torssell in H. Steinberg and A. L. McCloskey (Ed): Progress in Boron Chemistry, 1, (1964) 369 and R. Köster in Houben-Weyl, Methoden der Organischen Chemie, Vol. 13/3a, 4th Edition 1982, 617 et seq.).

Unless otherwise indicated, all above-described processes are expediently carried out under atmospheric pressure or under the inherent pressure of the reaction mixture in question.

As a rule, the reaction mixtures are worked up by methods known per se, for example by removing the solvent, partitioning the residue in a mixture of water and a suitable organic solvent, and working up the organic phase to obtain the product.

Those starting compounds which are given for the individual processes which are already known can be obtained in a manner known per se, for example also by one of the processes described.

The substituted 2-phenylpyridines of the formula I can contain one or more chiral centers, in which case they are obtained, as a rule, as mixtures of enantiomers or diastereomers. If desired, the mixtures can be separated to give the essentially pure isomers by methods which are customary for this purpose, for example by means of crystallization or chromatography on an optically active adsorbate. Alternatively, pure optically active isomers can be prepared from corresponding, optically active starting materials.

Substituted 2-phenylpyridines I having CH-acidic substituents can be converted into their salts, preferably their alkali metal salts, in a manner known per se.

Salts of I whose metal ion is not an alkali metal ion can be prepared by double decomposition of the corresponding alkali metal salt in a conventional manner, also ammonium, phosphonium, sulfonium and sulfoxonium salts by means of ammonia, phosphonium hydroxides, sulfonium hydroxides or sulfoxonium hydroxides.

Compounds I which have attached to them a terminal amino group can furthermore form acid addition salts. Suitable salts are, (generally, the salts of those acids which also have no adverse effect on the herbicidal or desiccant/defoliant action of I, eg., the hydrochlorides and hydrobromides, sulfates, nitrates, phosphates, oxalates or the dodecylbenzenesulfonates.

The compounds I/I' and their agriculturally useful salts, in the form of isomer mixtures and also in the form of the pure isomers, are suitable as herbicides. They are capable of effecting very good control of broad-leaf weeds and grass weeds in crops such as wheat, rice, corn, soybean and cotton, without harming the crop plants substantially. This effect can mainly be observed at low rates of application.

Depending on the application method in question, the compounds I/I', or herbicidal compositions comprising them, can also be employed in a further number of crop plants for removing undesirable plants. Suitable crops are, for example, the following:

Allium cepa, Ananas comosus, Arachis hypogaea, Asparagus officinalis, Beta vulgaris ssp. altissima, Beta vulgaris ssp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N.rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera and Zea mays.

Moreover, the compounds I/I' can be employed in crops which have been made essentially resistant to the action of I/I' by breeding and/or by means of genetic engineering methods.

Furthermore, the substituted 2-phenylpyridines I/I' are also suitable for the desiccation and/or defoliation of plants.

As desiccants, they are particularly suitable for desiccating the aerial parts of crop plants such as potatoes, oilseed rape, sunflower and soybean. This allows completely mechanical harvesting of these important crop plants.

Also of economic interest is facilitating harvesting, which is made possible in citrus fruit, olives or other species and varieties of pomaceous fruit, stone fruit and hard-shelled fruit by concentrated, over time, dehiscence or reducing the adhesion to the tree. The same mechanism, ie. promotion of the formation of abscission tissue between fruit or leaf portion and shoot portion of the plants is also essential for good regulation of defoliation in crop plants, in particular cotton.

Moreover, the shortened period of time within which the individual cotton plants ripen increases the fiber quality post-harvest.

The compounds I/I' or the herbicidal compositions comprising them can be used, for example, in the form of ready-to-spray aqueous solutions, powders, suspensions, also high-percentage aqueous, oily or other suspensions or dispersions, emulsions, oil dispersions, pastes, dusts, materials for broadcasting or granules by means of spraying, atomizing, dusting, spreading or pouring. The application forms depend on the intended uses; in any case, they should guarantee the finest possible distribution of the active ingredients according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols, such as methanol, ethanol, propanol, butanol and cyclohexanol, ketones, such as cyclohexanone, strongly polar solvents, eg. amines, such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substrates as such, or dissolved in an oil or solvent, can be homogenized in water by means of wetting agents, adhesives, dispersants or emulsifiers. However, it is also possible to prepare concentrates composed of active ingredient, (wetting agent, adhesive, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, eg. lignosulfonic acid, phenolsulfonic acid, naphthalenesulfonic acid and dibutylnaphthalenesulfonic acid, and of fatty acids, alkylsulfonates, alkylarylsulfonates, alkyl sulfates, lauryl ether sulfates, and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of naphthalenesulfonic acids with phenol and formaldehyde, polyoxyethylene octyl phenol ether, ethoxylated isooctylphenol, octylphenol or nonylphenol, alkylphenyl and tributylphenyl polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin sulfite waste liquors or methylcellulose.

Powders, materials for spreading and dusts can be prepared by mixing or concomitantly grinding the active ingredients with a solid carrier.

Granules, eg. coated granules, impregnated granules and homogeneous granules, can be prepared by binding the active ingredients to solid carriers. Solid carriers are mineral earths, such as silicic acids, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powder, or other solid carriers.

The concentrations of the active ingredients I/I' in the ready-to-use preparations can be varied within wide ranges, for example between 0.01 and 95% by weight, preferably between 0.5 and 90% by weight. The active ingredients are employed in a purity of 90% to 100%, preferably 95% to 100% (according to NMR spectrum).

The formulation examples which follow illustrate the preparation of such products:

I. 20 parts by weight of the compound No. Ic.019 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring into and finely distributing the solution in 100,000 parts by weight of water gives an aqueous dispersion which comprises 0.02% by weight of the active ingredient.

II. 20 parts by weight of the compound No. Ic.019 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring into and finely distributing the solution in 100,000 parts by weight of water gives an aqueous dispersion which comprises 0.02% by weight of the active ingredient.

III. 20 parts by weight of the active ingredient No. Ic.019 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring into and finely distributing the solution in 100,000 parts by weight of water gives an aqueous dispersion which comprises 0.02% by weight of the active ingredient.

IV. 20 parts by weight of the active ingredient No. Ic.019 are mixed thoroughly with 3 parts by weight of sodium diisobutylnaphthalene-$\alpha$-sulfonate, 17 parts by weight of a sodium lignosulfonate from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of the active ingredient No. Ic.019 are mixed with 97 parts by weight of finely divided kaolin. This gives a dust which comprises 3% by weight of the active ingredient.

VI. 20 parts by weight of the active ingredient No. Ic.019 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

The active ingredients I, or the herbicidal compositions, can be applied pre-emergence or post-emergence. If the active ingredients are less well tolerated by certain crop plants, application techniques may be used where the herbicidal compositions are sprayed, with the aid of the spraying equipment, in such a way that they come into as little contact as possible with the leaves of the sensitive crop plants, while the active ingredients reach the leaves of undesirable plants which grow under these crop plants, or the naked soil surface (post-directed, lay-by).

Depending on the control target, the season, the target plants and the growth stage, the application rates of active ingredient I/I' are 0.001 to 3.0, preferably 0.01 to 1, kg/ha of active ingredient (a.i.).

To broaden the spectrum of action and to achieve synergistic effects, the substituted 2-phenylpyridines I/I' may be mixed with a large number of representatives of other groups of herbicidal or growth-regulating active ingredients and applied jointly. Examples of suitable components for mixtures are diazines, 4H-3,1-benzoxazine derivatives, benzothiadiazinones, 2,6-dinitroanilines, N-phenylcarbamates, thiocarbamates, halo carboxylic acids, triazines, amides, ureas, diphenyl ethers, triazinones, uracils, benzofuran derivatives, cyclohexane-1,3-dione derivatives which have attached to them in the 2-position for example a carboxyl or carbimino group, quinolinecarboxylic acid derivatives, imidazolinones, sulfonamides, sulfonylureas, aryloxy- or heteroaryloxy-phenoxypropionic acids and their salts, esters and amides, and others.

It may furthermore be useful to apply the compounds I/I', alone or in combination with other herbicides, jointly as a mixture with further crop protection products, for example with compositions for controlling pests or phytopathogenic fungi or bacteria. Also of interest is the miscibility with mineral salt solutions, which are employed for treating nutrient and trace element deficiencies. Non-phytotoxic oils and oil concentrates may also be added.

PREPARATION EXAMPLES

3-Chloro-2-(4-[4-methyl-2-(1-methylmethoxycarbonylmethoxy)benzyloxy]phenyl)-5-trifluoromethylpyridine (No. Ic.019)

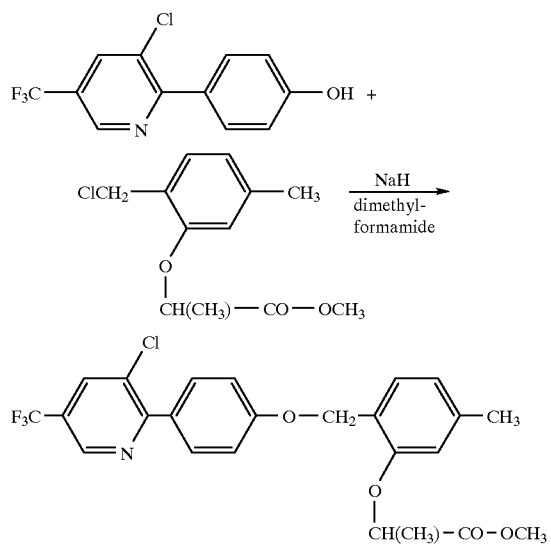

2.5 g of a 80% by weight suspension of sodium hydride in mineral oil were suspended in 30 ml of anhydrous dimethylformamide. A solution of 12.3 g of 3-chloro-2-(4-hydroxyphenyl)-5-trifluoromethylpyridine (disclosed in DE-A 43 23 916) in 150 ml of anhydrous dimethylformamide was added dropwise to this suspension in the course of 30 minutes, whereupon stirring was continued for 10 minutes. A solution of 12.1 g of methyl 2-(2-chloromethyl-5-methylphenoxy)propionate in 50 ml of anhydrous dimethylformamide were subsequently added dropwise to the reaction mixture in the course of 10 minutes. The mixture was then stirred for eight hours at 80° C and for 24 hours at 23° C. Most of the solvent was subsequently evaporated. The residue was stirred into 1.5 l of water, whereupon the aqueous phase was extracted three times using in each case 200 ml of methyl tert-butyl ether.

After the combined organic phases had been washed with 100 ml of water, they were dried over sodium sulfate and then concentrated. The crude product was purified by means of chromatography on silica gel using cyclohexane/ethyl acetate (4:1) as the eluent.

Yield: 11.1 g (52%) of white crystals; melting point: 117–119° C.

$^1$H NMR (270 MHz, in CDCl$_3$): δ [ppm]=1.65(d,3H), 2.33(s,3H), 3.76(s,3H), 4.85(q,1H), 5.20(d,1H), 5.30(d,1H), 6.60(s,1H), 6.83s(d,1H), 7.13(d,2H), 7.35(d,1H), 7.77(d, 2H), 8.00(s,1H), 8.82(s,1H).

The following compounds I according to the invention were prepared by a similar method:

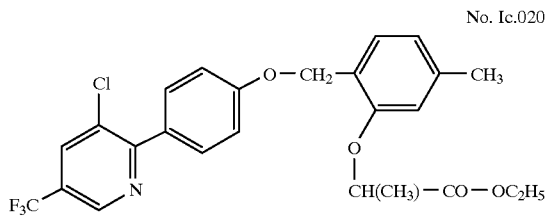

No. Ic.020

$^1$H NMR (250 MHz, in CDCl$_3$): δ [ppm]=1.15(t,3H), 1.62(d,3H), 2.31(s,3H), 4.23(q,2H), 4.83(q,1H), 5.20(d,1H), 5.32(d,1H), 6.60(s,1H), 6.80(d,1H), 7.12(d,2H), 7.37(d,1H), 7.78(d,2H), 8.00(s,1H), 8.81(s,1H).

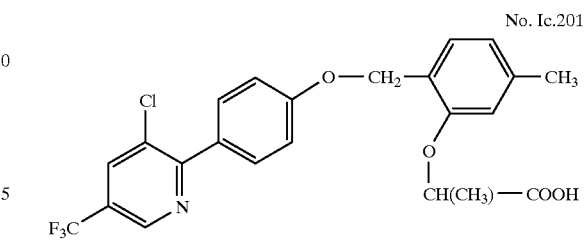

No. Ic.201

$^1$H NMR (250 MHz, in d$^6$-dimethyl sulfoxide): δ [ppm]= 1.53(d,3H), 2.28(s,3H), 4.92(q,1H), 5.20(s,2H), 6.78(s,1H), 6.81(d,1H), 7.15(d,2H), 7.29(d,1H), 7.74(d,2H), 8.54(s,1H), 9.00(s,1H).

USE EXAMPLES

Herbicidal Activity

The herbicidal action of the substituted 2-phenylpyridines I/I' was demonstrated by the following greenhouse experiments:

plastic flower pots containing loamy sand with approximately 3.0% of humus as substrate were used as culture containers. The seeds of the test plants were sown separately according to species.

For the pre-emergence treatment, the active ingredients which were suspended or emulsified in water were applied directly after sowing by means of finely-distributing nozzles. The containers were irrigated gently to promote germination and growth and subsequently covered with transparent plastic hoods until the plants had rooted. This cover causes uniform germination of the test plants, unless this was adversely affected by the active ingredients.

For the post-emergence treatment, the test plants were first grown to a height of 3 to 15 cm, depending on their growth form, and only then treated with the active ingredients which were suspended or emulsified in water. The test plants were either sown directly and grown on in the same containers or they were first grown separately as seedlings and transplanted to the test containers a few days prior to treatment. The application rate for the post-emergence treatment was 0.125 or 0.0625 kg/ha a.i. (active ingredient).

Depending on the species, the plants were kept at from 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants or complete destruction of at least the aerial parts, and 0 means no damage or normal course of growth.

The plants used in the greenhouse experiments were composed of the following species:

| Scientific Name | Common Name |
| --- | --- |
| Abutilon theophrasti | velvet leaf |
| Ipomoea subspecies | morningglory |
| Solanum nigrum | black nightshade |
| Veronica subspecies | speedwell |

At an application rate of 0.125 or 0.0625 kg/ha of a.i., the compound No. Ic.019 showed a very good action against the abovementioned plants when treated post-emergence.

USE EXAMPLES

Desiccant/Defoliant Activity

The test plants used were young cotton plants with 4 leaves (without cotyledons) which had been grown under greenhouse conditions (relative humidity 50 to 70%; day/night temperature 27/20° C.).

The leaves of the young cotton plants were treated to runoff point with aqueous preparations of the active ingredients (with the addition of 0.15% by weight, based on the spray mixture, of the fatty alcohol alkoxylate Plurafac LF 700). The amount of water applied was 1000 l/ha (converted). After 13 days, the number of shed leaves and the degree of defoliation was determined in %.

No leaves were shed in the untreated control plants.

We claim:

1. A substituted 2-phenylpyridine of the general formula I

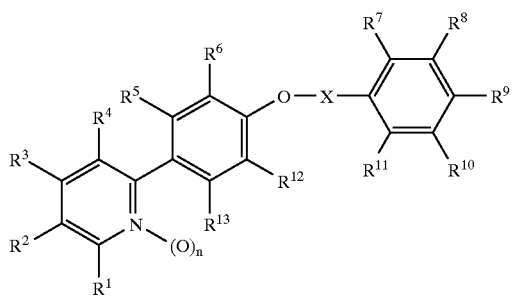

where the variables have the following meanings:

n is 0 or 1;
$R^1$ and $R^3$ are hydrogen;
$R^2$ is $C_1$–$C_4$-haloalkyl;
$R^4$ is halogen;
$R^5$ is hydrogen, halogen or cyano;
$R^6$ and $R^{13}$ independently of one another are hydrogen or halogen;
X is methylene or carbonyl;
$R^7$, $R^8$, $R^9$, $R^{10}$ independently of one another are hydrogen, halogen, $C_1$–$C_4$-alkyl, $C_1$–$C_4$-alkoxy or nitro;
$R^{11}$ is hydrogen, halogen, $C_1$–$C_4$-alkyl, $C_1$–$C_4$-haloalkyl, $C_1$–$C_4$-hydroxyalkyl, $C_1$–$C_4$-alkoxy-$C_1$–$C_4$-alkyl, $C_3$–$C_6$-cycloalkyl, $C_2$–$C_4$-alkenyl, $C_2$–$C_4$-alkynyl, hydroxycarbonyl-$C_1$–$C_4$-alkyl, hydroxycarbonyl-$C_2$–$C_4$-alkenyl, hydroxycarbonyl-$C_2$–$C_4$-alkynyl, ($C_1$–$C_4$-alkoxy)carbonyl-$C_1$–$C_4$-alkyl, ($C_1$–$C_4$-alkoxy)carbonyl-$C_2$–$C_4$-alkenyl, ($C_1$–$C_4$-alkoxy)carbonyl-$C_2$–$C_4$-alkynyl, ($C_1$–$C_4$-alkoxy)carbonyl-$C_2$–$C_4$-haloalkyl, ($C_1$–$C_4$-alkoxy)carbonyl-$C_2$–$C_4$-haloalkenyl, aminocarbonyl-$C_1$–$C_4$-alkyl, aminocarbonyl-$C_2$–$C_4$-alkenyl, aminocarbonyl-$C_2$–$C_4$-alkynyl, $C_1$–$C_4$-alkylaminocarbonyl-$C_1$–$C_4$-alkyl, $C_1$–$C_4$-alkylaminocarbonyl-$C_2$–$C_4$-alkenyl, $C_1$–$C_4$-alkylaminocarbonyl-$C_2$–$C_4$-alkynyl, di($C_1$–$C_4$-alkyl)aminocarbonyl-$C_1$–$C_4$-alkyl, di($C_1$–$C_4$-alkyl)aminocarbonyl-$C_2$–$C_4$-alkenyl, di($C_1$–$C_4$-alkyl)aminocarbonyl-$C_2$–$C_4$-alkynyl, aminocarbonyl-$C_1$–$C_4$-haloalkyl, aminocarbonyl-$C_2$–$C_4$-haloalkenyl, $C_1$–$C_4$-alkylaminocarbonyl-$C_1$–$C_4$-haloalkyl, $C_1$–$C_4$-alkylaminocarbonyl-$C_2$–$C_4$-haloalkenyl, di($C_1$–$C_4$-alkyl)aminocarbonyl-$C_2$–$C_4$-haloalkyl, di($C_1$–$C_4$-alkyl)aminocarbonyl-$C_2$–$C_4$-haloalkenyl, (hydroxycarbonyl-$C_1$–$C_4$-alkyl)aminocarbonyl-$C_2$–$C_4$-alkenyl, (hydroxycarbonyl-$C_1$–$C_4$-alkyl)aminocarbonyl-$C_2$–$C_4$-haloalkenyl, N-(hydroxycarbonyl-$C_1$–$C_4$-alkyl)-N-($C_1$–$C_4$-alkyl)aminocarbonyl-$C_2$–$C_4$-alkenyl, N-(hydroxycarbonyl-$C_1$–$C_4$-alkyl)-N-($C_1$–$C_4$-alkyl)aminocarbonyl-$C_2$–$C_4$-haloalkenyl, [($C_1$–$C_4$-alkoxy)carbonyl-$C_1$–$C_4$-alkyl]-aminocarbonyl-$C_2$–$C_4$-alkenyl, [($C_1$–$C_4$-alkoxy)carbonyl-$C_1$–$C_4$-alkyl]aminocarbonyl-$C_2$–$C_4$-haloalkenyl, N-[($C_1$–$C_4$-alkoxy)carbonyl-$C_1$–$C_4$-alkyl]-N-($C_1$–$C_4$-alkyl)aminocarbonyl-$C_2$–$C_4$-alkenyl, N-[($C_1$–$C_4$-alkoxy)carbonyl-$C_1$–$C_4$-alkyl]-N-($C_1$–$C_4$-alkyl)aminocarbonyl-$C_2$–$C_4$-haloalkenyl, 2-[($C_1$–$C_4$-alkoxy)carbonyl]-pyrrolidin-1-yl-carbonyl-$C_2$–$C_4$-alkenyl, 2-[($C_1$–$C_4$-alkoxy)carbonyl]-pyrrolidin-1-ylcarbonyl-$C_2$–$C_4$-haloalkenyl, formyl, ($C_1$–$C_4$-alkyl)carbonyl, ($C_1$–$C_4$-haloalkyl)carbonyl, hydroxyimino-$C_1$–$C_4$-alkyl, $C_1$–$C_4$-alkoxyimino-$C_1$–$C_4$-alkyl, 1,1-di($C_1$–$C_4$-alkoxy)-$C_1$–$C_4$-alkyl, 1,1-di($C_1$–$C_4$-alkylthio)-$C_1$–$C_4$-alkyl,
nitro, hydroxylamino, amino, $C_1$–$C_4$-alkylamino, $C_3$–$C_6$-cycloalkylamino, di($C_1$–$C_4$-alkyl)amino, ($C_1$–$C_4$-alkyl)carbonylamino, ($C_1$–$C_4$-haloalkyl)carbonylamino, $C_1$–$C_4$-alkylsulfonylamino, di($C_1$–$C_4$-alkylsulfonyl)amino, $C_1$–$C_4$-haloalkylsulfonylamino, hydroxyl, $C_1$–$C_4$-alkoxy, $C_1$–$C_4$-haloalkoxy, cyano-$C_1$–$C_4$-alkoxy, $C_1$–$C_4$-alkoxy-$C_1$–$C_4$-alkoxy, $C_1$–$C_4$-alkylthio-$C_1$–$C_4$-alkoxy, $C_3$–$C_6$-cycloalkoxy, $C_2$–$C_4$-alkenyloxy, $C_2$–$C_4$-alkynyloxy, hydroxycarbonyl-$C_1$–$C_4$-alkoxy, ($C_1$–$C_6$-alkoxy)carbonyl-$C_1$–$C_4$-alkoxy, $C_1$–$C_4$-alkoxy-($C_1$–$C_4$-alkoxy)carbonyl-$C_1$–$C_4$-alkoxy, ($C_1$–$C_4$-alkoxy)carbonyl-($C_1$–$C_4$-alkoxy)carbonyl-$C_1$–$C_4$-alkoxy, aminocarbonyl-$C_1$–$C_4$-alkoxy, $C_1$–$C_4$-alkylaminocarbonyl-$C_1$–$C_4$-alkoxy, di($C_1$–$C_4$-alkyl)aminocarbonyl-$C_1$–$C_4$-alkoxy, 1-pyrrolidinylcarbonyl-$C_1$–$C_4$-alkoxy, 1-piperidinyl-carbonyl-$C_1$–$C_4$-alkoxy, 4-morpholinylcarbonyl-$C_1$–$C_4$-alkoxy, aminocarbonyl-($C_1$–$C_4$-alkoxy)carbonyl-$C_1$–$C_4$-alkoxy, ($C_1$–$C_4$-alkyl)aminocarbonyl-($C_1$–$C_4$-alkoxy)carbonyl-$C_1$–$C_4$-alkoxy, di($C_1$–$C_4$-alkyl)aminocarbonyl-($C_1$–$C_4$-alkoxy)carbonyl-$C_1$–$C_4$-alkoxy, -pyrrolidinyl-carbonyl-($C_1$–$C_4$-alkoxy)

carbonyl-$C_1$–$C_4$-alkoxy, 1-piperidinylcarbonyl-($C_1$–$C_4$-alkoxy)carbonyl-$C_1$–$C_4$-alkoxy, 4-morpholinylcarbonyl-($C_1$–$C_4$-alkoxy)carbonyl-$C_1$–$C_4$-alkoxy, [($C_1$–$C_4$-alkoxy)carbonyl-$C_1$–$C_4$-alkyl]aminocarbonyl-$C_1$–$C_4$-alkoxy, N-[($C_1$–$C_4$-alkoxy)carbonyl-$C_1$–$C_4$-alkyl]-N-($C_1$–$C_4$-alkyl)aminocarbonyl-$C_1$–$C_4$-alkoxy, [2-[($C_1$–$C_4$-alkoxy)carbonyl]pyrrolidin-1-yl]carbonyl-$C_1$–$C_4$-alkoxy, cyano, hydroxycarbonyl, COCl, ($C_1$–$C_4$-alkoxy)carbonyl, ($C_1$–$C_4$-haloalkoxy)carbonyl, $C_1$–$C_4$-alkoxy-($C_1$–$C_4$-alkoxy)carbonyl, aminocarbonyl, $C_1$–$C_4$-alkylaminocarbonyl, di($C_1$–$C_4$-alkyl)aminocarbonyl, $C_3$–$C_6$-cycloalkylaminocarbonyl, 1-pyrrolidinylcarbonyl, 1-piperidinylcarbonyl, 4-morpholinylcarbonyl, hydroxycarbonyl-$C_1$–$C_4$-alkylaminocarbonyl, N-(hydroxycarbonyl-$C_1$–$C_4$-alkyl)-N-($C_1$–$C_4$-alkyl)-aminocarbonyl, ($C_1$–$C_4$-alkoxy)carbonyl-$C_1$–$C_4$-alkylaminocarbonyl, N-[($C_1$–$C_4$-alkoxy)carbonyl-$C_1$–$C_4$-alkyl]-N-($C_1$–$C_4$-alkyl)aminocarbonyl, 2-hydroxycarbonylpyrrolidin-1-yl-carbonyl, 2-[($C_1$–$C_4$-alkoxy)carbonyl]pyrrolidin-1-yl-carbonyl or a group

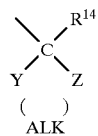

where
Y and Z independently of one another are oxygen or sulfur,
$R^{14}$ is hydrogen, $C_1$–$C_4$-alkyl or ($C_1$–$C_4$-alkoxy)carbonyl and
Alk is an ethylene or trimethylene chain where one or more hydrogen atoms can be replaced in each case by $C_1$–$C_4$-alkyl or ($C_1$–$C_4$-alkoxy)carbonyl;

$R^{12}$ is hydrogen, nitro, amino, hydroxylamino, $C_1$–$C_4$-alkylsulfonylamino, di($C_1$–$C_4$-alkylsulfonyl)amino, $C_1$–$C_4$-haloalkylsulfonylamino, ($C_1$–$C_4$-alkoxy)carbonyl-$C_1$–$C_4$-haloalkyl or ($C_1$–$C_4$-alkoxy)carbonyl-$C_2$–$C_4$-haloalkenyl;

with the proviso that $R^5$, $R^7$, $R^{11}$ and $R^{13}$ are not all simultaneously hydrogen or $R^7$ and $R^8$ or $R^{10}$ and $R^{11}$ are not simultaneously fluorine, or an agriculturally useful salt thereof.

2. A herbicidal composition which comprises a herbicidally active amount of at least one compound of claim 1, and at least one inert liquid and/or solid carrier.

3. A composition for desiccating and/or defoliating plants which comprises such an amount of at least one substituted 2-phenylpyridine of the formula I as defined in claim 1 or of an agriculturally useful salt of I that it acts as a desiccant or defoliant, and at least one inert liquid and/or solid carrier and, if desired, at least one adjuvant.

4. A method of controlling undesirable vegetation, which comprises allowing a herbicidally active amount of at least one substituted 2-phenylpyridine of the claim 1, to act on plants, their environment or seeds.

5. A method of desiccating and/or defoliating plants, which comprises allowing such an amount, that acts as a desiccant and/or defoliant, of at least one substituted 2-phenylpyridine of claim 1, to act on plants.

6. A method as claimed in claim 5, wherein cotton is treated.

* * * * *

UNITED STATES PATENT AND TRADEMARK OFFICE
CERTIFICATE OF CORRECTION

PATENT NO.: 5,958,837

DATED: September 28, 1999

INVENTOR(S): SCHAEFER et al.

It is certified that error appears in the above-identified patent and that said Letters Patent is hereby corrected as shown below:

Col. 36, claim 1, line 67, "-pyrrolidinyl-" should be --1-pyrrolidinyl- --.

Signed and Sealed this

Sixteenth Day of May, 2000

*Attest:*

Q. TODD DICKINSON

*Attesting Officer*      *Director of Patents and Trademarks*